(12) United States Patent
Franklin et al.

(10) Patent No.: US 12,102,330 B2
(45) Date of Patent: Oct. 1, 2024

(54) VASCULAR OCCLUSION CATHETER FOR PARTIAL OCCLUSION OR FULL OCCLUSION

(71) Applicant: Prytime Medical Devices, Inc., Boerne, TX (US)

(72) Inventors: Curtis J. Franklin, Lakewood, CO (US); Gregory S. Schmid, Boerne, TX (US); Mathew Charles Pickering, Boerne, TX (US)

(73) Assignee: PRYTIME MEDICAL DEVICES, INC., Boerne, TX (US)

( * ) Notice: Subject to any disclaimer, the term of this patent is extended or adjusted under 35 U.S.C. 154(b) by 0 days.

(21) Appl. No.: 17/800,487

(22) PCT Filed: Mar. 17, 2022

(86) PCT No.: PCT/US2022/020704
§ 371 (c)(1),
(2) Date: Sep. 22, 2022

(87) PCT Pub. No.: WO2022/197895
PCT Pub. Date: Sep. 22, 2022

(65) Prior Publication Data
US 2023/0414221 A1  Dec. 28, 2023

Related U.S. Application Data

(60) Provisional application No. 63/276,711, filed on Nov. 8, 2021, provisional application No. 63/162,933, filed on Mar. 18, 2021.

(51) Int. Cl.
*A61B 17/12* (2006.01)
*A61M 25/00* (2006.01)
*A61B 17/00* (2006.01)

(52) U.S. Cl.
CPC .. *A61B 17/12136* (2013.01); *A61B 17/12031* (2013.01); *A61B 17/12036* (2013.01);
(Continued)

(58) Field of Classification Search
CPC ........ A61B 17/12136; A61B 17/12031; A61B 17/12036; A61B 17/12109;
(Continued)

(56) References Cited

U.S. PATENT DOCUMENTS 2,156,289 A  5/1939  Hoy
4,464,172 A  8/1984  Lichtenstein
(Continued)

FOREIGN PATENT DOCUMENTS

EP  1094861 B1  4/2005
EP  1658808 A1  5/2006
(Continued)

OTHER PUBLICATIONS

Extended Search Report issued May 10, 2023 in European Application No. 22743436.2.
(Continued)

*Primary Examiner* — Brooke Labranche
(74) *Attorney, Agent, or Firm* — Panitch Schwarze Belisario & Nadel LLP

(57) ABSTRACT

A vascular occlusion catheter for partial occlusion or full occlusion includes a proximal outer shaft, a distal outer shaft, and an occlusion balloon therebetween. The proximal shaft has first and second internal lumens, the first internal lumen being in fluid communication with the balloon. The distal shaft has a distal internal lumen. A hypotube extends through the first internal lumen, through the balloon and into communication with the distal internal lumen. A first window is formed in the proximal shaft and a proximal sensor is positioned within the second internal lumen at the win-
(Continued)

dow. A second window is formed in the distal shaft and a distal sensor is positioned within the distal internal lumen at the window. A display hub is positioned along the proximal shaft and electrically connected with the sensors The uninflated vascular occlusion catheter has a greatest outer diameter of seven French or less.

20 Claims, 30 Drawing Sheets

(52) U.S. Cl.
CPC ... *A61B 17/12109* (2013.01); *A61M 25/0026* (2013.01); *A61M 25/008* (2013.01); *A61B 2017/00115* (2013.01); *A61M 2025/0004* (2013.01); *A61M 2205/502* (2013.01); *A61M 2230/30* (2013.01)

(58) Field of Classification Search
CPC ..... A61B 2017/00115; A61M 25/0026; A61M 25/008; A61M 2025/0004; A61M 2205/502; A61M 2230/30
See application file for complete search history.

(56) References Cited

U.S. PATENT DOCUMENTS

| | | | |
|---|---|---|---|
| 4,713,888 A | 12/1987 | Broselow |
| 4,777,951 A | 10/1988 | Cribier et al. |
| 4,823,469 A | 4/1989 | Broselow |
| 4,865,549 A | 9/1989 | Sonsteby |
| 4,926,885 A | 5/1990 | Hinkle |
| 4,983,166 A | 1/1991 | Yamawaki |
| 5,047,045 A | 9/1991 | Arney et al. |
| 5,087,246 A | 2/1992 | Smith |
| 5,135,494 A | 8/1992 | Engelson et al. |
| 5,158,529 A | 10/1992 | Kanai |
| 5,169,386 A | 12/1992 | Becker et al. |
| 5,250,070 A | 10/1993 | Parodi |
| 5,282,479 A | 2/1994 | Havran |
| 5,295,995 A | 3/1994 | Kleiman |
| 5,320,605 A | 6/1994 | Sahota |
| 5,383,856 A | 1/1995 | Bersin |
| 5,425,711 A | 6/1995 | Ressemann |
| 5,447,503 A | 9/1995 | Miller |
| 5,505,702 A | 4/1996 | Arney |
| 5,522,400 A | 6/1996 | Williams |
| 5,554,121 A | 9/1996 | Ainsworth |
| 5,558,644 A | 9/1996 | Boyd et al. |
| 5,571,093 A | 11/1996 | Cruz et al. |
| 5,609,606 A | 3/1997 | O'Boyle |
| 5,718,678 A | 2/1998 | Fleming, III |
| 5,738,652 A | 4/1998 | Boyd et al. |
| 5,911,702 A | 6/1999 | Romley et al. |
| 6,007,517 A | 12/1999 | Anderson |
| 6,011,988 A | 1/2000 | Lynch et al. |
| 6,013,019 A | 1/2000 | Fischell et al. |
| 6,013,055 A | 1/2000 | Bampos et al. |
| 6,102,930 A | 8/2000 | Simmons, Jr. |
| 6,113,579 A | 9/2000 | Eidenschink et al. |
| 6,129,737 A | 10/2000 | Hamilton et al. |
| 6,146,370 A | 11/2000 | Barbut |
| 6,161,547 A | 12/2000 | Barbut |
| 6,165,199 A | 12/2000 | Barbut |
| 6,190,356 B1 | 2/2001 | Bersin |
| 6,231,572 B1 | 5/2001 | Hart et al. |
| 6,248,121 B1 | 6/2001 | Nobles |
| 6,280,434 B1 | 8/2001 | Kinoshita et al. |
| 6,423,031 B1 | 7/2002 | Donlon |
| 6,453,572 B2 | 9/2002 | Cross et al. |
| 6,575,932 B1 | 6/2003 | O'Brien et al. |
| 6,579,221 B1 | 6/2003 | Peterson |
| 6,602,270 B2 | 8/2003 | Leschinsky et al. |
| 6,656,153 B1 | 12/2003 | Sakai et al. |
| 6,666,814 B2 | 12/2003 | Downey et al. |
| 6,669,679 B1 | 12/2003 | Savage et al. |
| 6,679,860 B2 | 1/2004 | Stiger |
| 6,695,811 B2 | 2/2004 | Samson et al. |
| 6,719,270 B2 | 4/2004 | Ozawa |
| 6,719,720 B1 | 4/2004 | Voelker et al. |
| 6,733,513 B2 | 5/2004 | Boyle et al. |
| 6,735,532 B2 | 5/2004 | Freed et al. |
| 6,736,790 B2 | 5/2004 | Barbut et al. |
| 6,746,462 B1 | 6/2004 | Selmon et al. |
| 6,796,959 B2 | 9/2004 | Davis et al. |
| 6,936,056 B2 | 8/2005 | Nash et al. |
| 6,979,318 B1 | 12/2005 | McDonald et al. |
| 7,341,571 B1 | 3/2008 | Harris et al. |
| 7,434,326 B2 | 10/2008 | Gifford |
| 7,503,904 B2 | 3/2009 | Choi |
| 7,503,909 B2 | 3/2009 | Kusu et al. |
| 7,763,043 B2 | 7/2010 | Goodin et al. |
| 7,892,469 B2 | 2/2011 | Lim et al. |
| 7,909,810 B2 | 3/2011 | Noone |
| 7,951,186 B2 | 5/2011 | Eidenschink et al. |
| 7,951,819 B2 | 5/2011 | Niculescu-Duvaz et al. |
| 7,959,644 B2 | 6/2011 | Shriver |
| 8,021,330 B2 | 9/2011 | McAndrew |
| 8,088,103 B2 | 1/2012 | Teeslink et al. |
| 8,162,879 B2 | 4/2012 | Tattangadi et al. |
| 8,241,241 B2 | 8/2012 | Evans et al. |
| 8,262,611 B2 | 9/2012 | Teeslink et al. |
| 8,419,648 B2 | 4/2013 | Corl et al. |
| 8,430,899 B2 | 4/2013 | Dae et al. |
| 8,499,681 B2 | 8/2013 | Kanner et al. |
| 8,545,382 B2 | 10/2013 | Suzuki et al. |
| 8,655,798 B2 | 2/2014 | Humphrey et al. |
| 8,672,868 B2 | 3/2014 | Simons |
| 8,747,358 B2 | 6/2014 | Trombley, III et al. |
| 8,814,900 B2 | 8/2014 | Fleming, III |
| 8,900,214 B2 | 12/2014 | Nance et al. |
| 8,948,848 B2 | 2/2015 | Merhi |
| 8,951,565 B2 | 2/2015 | McCarthy |
| 9,131,874 B2 | 9/2015 | Eliason et al. |
| 9,211,396 B2 | 12/2015 | Aboytes |
| D748,257 S | 1/2016 | Franklin |
| 9,414,843 B2 | 8/2016 | Pavcnik et al. |
| 9,474,882 B2 | 10/2016 | Franklin et al. |
| 9,687,333 B2 | 6/2017 | Angel et al. |
| 10,368,872 B2 | 8/2019 | Franklin et al. |
| 2001/0038807 A1 | 11/2001 | Barbut et al. |
| 2002/0007146 A1 | 1/2002 | Omaleki et al. |
| 2002/0062119 A1 | 5/2002 | Zadno-Azizi |
| 2002/0081406 A1 | 6/2002 | Wang et al. |
| 2002/0193735 A1 | 12/2002 | Stiger |
| 2003/0032974 A1 | 2/2003 | Leschinsky et al. |
| 2003/0083579 A1 | 5/2003 | Aita et al. |
| 2003/0167038 A1 | 9/2003 | Yozu et al. |
| 2004/0039332 A1 | 2/2004 | Kantor |
| 2004/0073162 A1 | 4/2004 | Bleam et al. |
| 2004/0082935 A1 | 4/2004 | Lee et al. |
| 2004/0254528 A1 | 12/2004 | Adams et al. |
| 2005/0059931 A1 | 3/2005 | Garrison et al. |
| 2005/0148812 A1 | 7/2005 | Nigroni et al. |
| 2005/0261725 A1 | 11/2005 | Crawford et al. |
| 2006/0100639 A1 | 5/2006 | Levin et al. |
| 2007/0043307 A1 | 2/2007 | Raulerson et al. |
| 2007/0043409 A1 | 2/2007 | Brian et al. |
| 2007/0129466 A1 | 6/2007 | Kagawa et al. |
| 2007/0135830 A1 | 6/2007 | Schaeffer |
| 2007/0219466 A1 | 9/2007 | Tremulis et al. |
| 2007/0219488 A1 | 9/2007 | Francescatti |
| 2008/0027356 A1 | 1/2008 | Chen et al. |
| 2008/0082046 A1 | 4/2008 | Kato et al. |
| 2008/0082119 A1 | 4/2008 | Vitullo |
| 2008/0097300 A1 | 4/2008 | Eskaros et al. |
| 2008/0200839 A1* | 8/2008 | Bunch .................. A61M 25/09 600/585 |
| 2008/0243067 A1 | 10/2008 | Rottenberg et al. |
| 2008/0243221 A1 | 10/2008 | Arcand |
| 2008/0262477 A1 | 10/2008 | Djaladat |
| 2008/0287786 A1 | 11/2008 | Lentz |
| 2009/0018500 A1 | 1/2009 | Carter et al. |

(56) References Cited

U.S. PATENT DOCUMENTS

| | | |
|---|---|---|
| 2009/0026595 A1 | 1/2009 | Kadoi |
| 2009/0062666 A1 | 3/2009 | Roteliuk |
| 2009/0171272 A1 | 7/2009 | Tegg et al. |
| 2009/0171293 A1 | 7/2009 | Yang et al. |
| 2009/0265951 A1 | 10/2009 | Black |
| 2009/0287079 A1 | 11/2009 | Shriver |
| 2009/0312807 A1 | 12/2009 | Boudreault et al. |
| 2010/0016735 A1 | 1/2010 | Harpas et al. |
| 2010/0041984 A1 | 2/2010 | Shapland et al. |
| 2010/0113939 A1 | 5/2010 | Mashimo et al. |
| 2010/0130810 A1 | 5/2010 | Mohl |
| 2010/0204712 A1 | 8/2010 | Mallaby |
| 2010/0234915 A1 | 9/2010 | Herlich et al. |
| 2010/0241008 A1* | 9/2010 | Belleville ............ A61B 5/0215 600/478 |
| 2010/0262076 A1 | 10/2010 | Rowe et al. |
| 2010/0268017 A1 | 10/2010 | Siess |
| 2010/0280451 A1 | 11/2010 | Teeslink et al. |
| 2011/0144742 A1 | 6/2011 | Madrid et al. |
| 2011/0172696 A1 | 7/2011 | Jeffrey et al. |
| 2011/0196412 A1 | 8/2011 | Levit et al. |
| 2011/0295301 A1 | 12/2011 | Hoem et al. |
| 2011/0295302 A1 | 12/2011 | Mohl |
| 2011/0301630 A1 | 12/2011 | Hendriksen et al. |
| 2012/0101413 A1 | 4/2012 | Beetel et al. |
| 2012/0108979 A1 | 5/2012 | Franklin et al. |
| 2012/0109057 A1 | 5/2012 | Krolik et al. |
| 2012/0116352 A1 | 5/2012 | Rangi |
| 2012/0130359 A1 | 5/2012 | Turovskiy |
| 2012/0172911 A1 | 7/2012 | Welch |
| 2012/0209176 A1 | 8/2012 | Anderson |
| 2012/0215166 A1 | 8/2012 | Barki |
| 2012/0271231 A1 | 10/2012 | Agrawal |
| 2012/0302994 A1 | 11/2012 | Wilson et al. |
| 2013/0102926 A1 | 4/2013 | Eliason et al. |
| 2013/0102929 A1 | 4/2013 | Haight et al. |
| 2013/0172786 A1 | 7/2013 | Olson et al. |
| 2013/0190619 A1 | 7/2013 | Nudel |
| 2013/0253467 A1 | 9/2013 | Gianotti et al. |
| 2013/0281869 A1 | 10/2013 | Barbut et al. |
| 2013/0289607 A1 | 10/2013 | Pedersen et al. |
| 2013/0338637 A1 | 12/2013 | Fischer, Jr. et al. |
| 2014/0221898 A1 | 8/2014 | Kurrus et al. |
| 2014/0243873 A1 | 8/2014 | Franklin |
| 2014/0249504 A1 | 9/2014 | Franklin et al. |
| 2014/0316012 A1 | 10/2014 | Freyman et al. |
| 2014/0364835 A1 | 12/2014 | Allen et al. |
| 2014/0378869 A1 | 12/2014 | Sela et al. |
| 2015/0012031 A1 | 1/2015 | Rago et al. |
| 2015/0039012 A1 | 2/2015 | Solar et al. |
| 2015/0157326 A1 | 6/2015 | Schiemanck et al. |
| 2015/0272732 A1 | 10/2015 | Tilson et al. |
| 2015/0367098 A1 | 12/2015 | Aggerholm et al. |
| 2016/0000446 A1 | 1/2016 | Eliason et al. |
| 2016/0051386 A1 | 2/2016 | Haarmann-Thiemann |
| 2016/0375230 A1 | 12/2016 | Lee et al. |
| 2019/0076152 A1* | 3/2019 | Franklin ............ A61M 25/1011 |
| 2019/0366046 A1 | 12/2019 | Klocke et al. |
| 2020/0022587 A1 | 1/2020 | Glover et al. |
| 2021/0138187 A1* | 5/2021 | Tilson ............... A61M 25/0102 |
| 2021/0282759 A1* | 9/2021 | Layman ............... A61M 25/09 |
| 2021/0290243 A1* | 9/2021 | Franklin .......... A61B 17/12109 |

FOREIGN PATENT DOCUMENTS

| | | |
|---|---|---|
| EP | 1911484 A2 | 4/2008 |
| EP | 2389974 A1 | 11/2011 |
| EP | 2716323 A1 | 4/2014 |
| EP | 2837402 A2 | 2/2015 |
| GB | 2297259 A | 7/1996 |
| JP | H 03198868 A | 8/1991 |
| JP | H03280962 A | 12/1991 |
| JP | H 09-164208 A | 6/1997 |
| JP | H1080497 A | 3/1998 |
| JP | 2000217922 A | 8/2000 |
| JP | 2002505165 A | 2/2002 |
| JP | 2003535652 A | 12/2003 |
| JP | 200714820 A | 1/2007 |
| JP | 2008546471 A | 12/2008 |
| JP | 2011245300 A | 12/2011 |
| WO | 9220398 A1 | 11/1992 |
| WO | 9713542 A1 | 4/1997 |
| WO | 9725093 A1 | 7/1997 |
| WO | 9834670 A2 | 8/1998 |
| WO | 1999/24105 A2 | 5/1999 |
| WO | 9925417 A1 | 5/1999 |
| WO | 9944666 A2 | 9/1999 |
| WO | 0197743 A2 | 12/2001 |
| WO | 2004049970 A2 | 6/2004 |
| WO | 2006014631 A1 | 2/2006 |
| WO | 2006135853 A2 | 12/2006 |
| WO | 2007001701 A1 | 1/2007 |
| WO | 2007022592 A1 | 3/2007 |
| WO | 2008013441 A1 | 1/2008 |
| WO | 2010070685 A1 | 6/2010 |
| WO | 2011133736 A2 | 10/2011 |
| WO | 2014/003809 A1 | 1/2014 |
| WO | 2014134215 A1 | 9/2014 |
| WO | 2014152191 A1 | 9/2014 |
| WO | 2015/006828 A1 | 1/2015 |
| WO | 2015035393 A1 | 3/2015 |
| WO | 2015191685 A1 | 12/2015 |
| WO | 2016149653 A2 | 9/2016 |
| WO | 2017210584 A1 | 12/2017 |
| WO | 2019095049 A1 | 5/2019 |
| WO | 2020033372 A1 | 2/2020 |

OTHER PUBLICATIONS

Int'l Search Report and Written Opinion issued Jun. 8, 2022 in Int'l Application No. PCT/US2022/020704.

Holcomb et al., "Causes of death in US Special Operations Forces in the global war on terrorism: 2001-2004," Annals of Surgery, vol. 245, No. 6, pp. 986-991 (2007).

Sohn et al., "Demographics, Treatment, and Early Outcomes in Penetrating Vascular Combat Trauma," Arch Surg, vol. 143, No. 8, pp. 783-787 (2008).

White et al., "The Epidemiology of Vascular Injury in the Wars in Iraq and Afghanistan," Annals of Surgery, vol. 253, No. 6, pp. 1184-1189 (2011).

Fenton et al., "Comparing risks of alternative medical diagnosis using Bayesian arguments," J. Biomed. Inf., vol. 43, pp. 485-495 (2010).

Patel et al., "Bayesian Designs for Device Clinical Trials," MDG Forum, Waltham, MA., Nov. 3, 2010, downloaded from web page: <http://www.cytel.com/pdfs/Patel_Bayes_Devices_Slides_11.18.10.pdf>.

Guidance for the Use of Bayesian Statistics in Medical Device Clinical Trials, U.S. Department of Health and Human Services, Food and Drug Administration, Center for Devices and Radiological Health, Division of Biostatistics, Office of Surveillance and Biometrics, Feb. 5, 2010.

Sandgren et al., "The Diameter of the Common Femoral Artery in Healthy Human: Influence of Sex, Age, and Body Size," Journal of Vascular Surgery, vol. 29, No. 3, pp. 503-510 (1999).

SAM II et al., "Blunt Traumatic Aortic Transection: Endoluminal Repair with Commercially Available Aortic Cuffs," Journal of Vascular Surgery, vol. 38, No. 5, pp. 1132-1135 (2003).

Peterson et al., "Percutaneous endovascular repair of blunt thoracic aortic transection," Journal of Trauma, vol. 59, No. 5, pp. 1062-1065 (2005).

Office Action issued Oct. 28, 2014 in U.S. Appl. No. 13/642,465, by Eliason.

Office Action issued Apr. 6, 2015 in U.S. Appl. No. 13/642,465, by Eliason.

Stannard et al., "Resuscitative Endovascular Balloon Occlusion of the Aorta (REBOA) as an Adjunct for Hemorrhagic Shock," J. Trauma, vol. 71, pp. 1869-1872 (2011).

(56) References Cited

OTHER PUBLICATIONS

Ledgerwood et al., "The Role of Thoracic Aortic Occlusion for Massive Hemoperitoneum," J Trauma, vol. 16, No. 8, pp. 610-615 (1976).
Detrano et al. "Bayesian Probability Analysis: a Prospective Demonstration of its Clinical Utility in Diagnosing Coronary Disease," Circulation, vol. 69, No. 3, pp. 541-547 (1984).
Langewouters et al., "The static elastic properties of 45 human thoracic and 20 abdominal aortas in vitra and the parameters of a new model," Journal of Biometrics, vol. 17, No. 6, pp. 425-435 (1984).
Hughes, "Use of an Intra-Aortic Balloon Catheter Tamponade for Controlling Intra-Abdominal Hemorrhage in Man," Surgery, vol. 36, pp. 65-68 (1954).
Office Action issued Aug. 23, 2016 in AU Application No. 2015274743.
Extended European Search Report issued Oct. 5, 2016 in Europe Application No. EP 14 75 6640.
Supplemental Search Report issued Dec. 19, 2016 in EP Application No. 15806534.
Extended Search Report issued Mar. 24, 2017 in EP Application No. 14842370.
Extended Search Report issued Mar. 21, 2017 in EP Application No. 15806534.
Office Action issued Apr. 11, 2017 in JP Application No. 2016-546035.
Office Action issued Mar. 20, 2017 in CA Application No. 2,797,237.
Extended European Search Report issued Jun. 26, 2017 in EP Application No. 14842370.
Office Action issued Sep. 19, 2017 in JP Application No. 2015-559309.
Office Action issued Sep. 12, 2017 in JP Application No. 2016-546035.
Office Action issued Oct. 12, 2017 in CA Application No. 2,980,018.
Chen et al., "The Renal Length Nomogram: A Multivariable Approach," The Journal of Urology, vol. 168, pp. 2149-2152 (Nov. 2002).
Office Action issued Aug. 27, 2018 in U.S. Appl. No. 14/917,286, by Franklin.
European Search Report Issued May 31, 2022 in European Application No. 19846055.2.
Office Action issued Jun. 20, 2023 in U.S. Appl. No. 17/563,669.
Int'l Preliminary Report on Patentability issued Sep. 28, 2023 in Int'l Application No. PCT/US22/20704.

\* cited by examiner

VASCULAR OCCLUSION CATHETER FOR PARTIAL OCCLUSION OR FULL OCCLUSION

CROSS-REFERENCE TO RELATED APPLICATIONS

This application claims priority from International Application No. PCT/US2022/020704, filed Mar. 17, 2022, which claims priority from similarly-titled U.S. Provisional Patent Application No. 63/162,933, filed Mar. 18, 2021, and similarly-titled U.S. Provisional Patent Application No. 63/276,711, filed Nov. 8, 2021, the entire contents of each of which are incorporated by reference herein.

STATEMENT REGARDING FEDERALLY SPONSORED RESEARCH OR DEVELOPMENT

This invention was made with government support under Contract No. W81XWH-20-1-0524 awarded by USA Medical Research Acquisition Activity. The government has certain rights in the invention.

BACKGROUND OF THE DISCLOSURE

The disclosure relates to vascular occlusions catheters and, more particularly, to vascular occlusion catheters capable of performing both partial and full vascular occlusion.

Vascular occlusion may be indicated in either the venous system and/or the arterial system. Endoarterial occlusion, such as, resuscitative endovascular balloon occlusion of the aorta ("REBOA"), is a procedure in which a blood vessel is at least partially occluded in order to restrict blood flow upstream or downstream of the occlusion site for purposes of a vascular procedure or repair. Partial occlusion of the aorta is beneficial to mitigate the risk of ischemia below the site of the occlusion to limit or eliminate lack of blood flow to organs and tissue below the occlusion location. That is, partial perfusion past the occlusion balloon can provide the benefits of focusing or directing a majority of blood flow to the brain, heart and lungs or other upstream portions of the patient, but also potentially increasing the amount of time the occlusion balloon can be implanted in the patient, by providing at least partial blood flow to the patient's organs downstream of the occlusion member, such as to the patient's liver, digestive tract, kidneys and legs.

Traditionally, an insertion cannula or sheath is utilized for introducing a catheter into a patient. The profile of the catheter directly corresponds to a profile of the sheath, and, in turn, the size of the access site incision. Any increase in the size or diameter of the catheter shaft results in an increase in size or counterpart dimension of the insertion sheath, and, accordingly, an increase in the access site incision in the patient's body to insert the catheter. A seven French (7 Fr) or smaller insertion sheath typically results in the access site through the patient's skin and into the target vessel being re-closed by holding manual pressure for a period of time, such as twenty to thirty minutes (20-30 min). If the insertion sheath has an inner diameter greater than seven French (7 Fr), surgical repair of the access site may be required, thereby further complicating the procedure.

It would, therefore, be desirable to further design, develop and implement an occlusion balloon catheter configured to at least partially occlude the target blood vessel while permitting partial perfusion to the patient's organs downstream thereof and minimizing the cross-sectional profile of the catheter to seven French (7 Fr) or less.

BRIEF SUMMARY OF THE DISCLOSURE

Briefly stated, one aspect of the present disclosure is directed to a vascular occlusion catheter having an inflatable occlusion balloon, a hypotube defining an internal hypotube lumen extending through the occlusion balloon, a proximal catheter shaft in fluid communication with the occlusion balloon and jacketing a portion of the hypotube proximal to the occlusion balloon, and a distal catheter shaft connected to the hypotube and the occlusion balloon and terminating in a distal, atraumatic tip.

In one configuration, the vascular occlusion catheter further includes at least one of a proximal MEMS sensor embedded in the proximal catheter shaft or a distal MEMS sensor embedded in the distal catheter shaft.

One aspect of the present disclosure is directed to a vascular occlusion catheter for at least partial occlusion of a target vessel having an internal vessel wall. The vascular occlusion catheter includes a proximal outer shaft; a distal outer shaft distally terminating with an atraumatic tip; and an occlusion balloon connected to the proximal outer shaft at a proximal neck and the distal outer shaft at a distal neck. The proximal outer shaft has a first internal lumen and a second internal lumen, the first internal lumen being in fluid communication with the occlusion balloon. The distal outer shaft has a distal internal lumen. A hypotube having an internal hypotube lumen extends through the first internal lumen, through the occlusion balloon and into communication with the distal internal lumen. The hypotube operates as the primary load-bearing chassis of the vascular occlusion catheter. A first window is formed in the proximal outer shaft and a proximal sensor is positioned within the second internal lumen facing the first window. A second window is formed in distal outer shaft and a distal sensor is positioned within the distal internal lumen facing the second window. A display hub is positioned along the proximal outer shaft, wherein the second internal lumen and the hypotube extend into the display hub, the display hub being electrically connected with the proximal sensor via the second internal lumen, and the display hub being electrically connected with the distal sensor via the internal hypotube lumen and the distal internal lumen. The occlusion balloon, the proximal outer shaft and the distal outer shaft have a greatest outer diameter of seven French (7 Fr) or less in an uninflated condition.

In one configuration, the proximal sensor may be a pressure sensor configured to measure central aortic pressure downstream of the occlusion balloon and the distal sensor may be a pressure sensor configured to measure central aortic pressure upstream of the occlusion balloon.

In any one of the previous configurations, the proximal sensor may be suspended in a first sensor case sealingly mounted in the second internal lumen, and the distal sensor may be suspended in a second sensor case sealingly mounted in the distal internal lumen.

In any one of the previous configurations, the vascular occlusion catheter may further include an inflation hub in fluid communication with the display hub, the first internal lumen also being in fluid communication with the display hub, wherein the inflation hub is fluidly connected with the first internal lumen within the display hub.

In any one of the previous configurations, the vascular occlusion catheter may further include a solid distal wire embedded in the distal outer shaft and extending toward the atraumatic tip, the solid distal wire tapering from a proximal end thereof to a distal end thereof. In one configuration, the solid distal wire may be constructed of nitinol. In one configuration, the solid distal wire may partially overlap, in a generally parallel arrangement, with the hypotube. In one configuration, a portion of the solid distal wire overlapping with the hypotube may be jacketed to the hypotube.

In any one of the previous configurations, the distal outer shaft may be at least partially constructed of a braided shaft.

In any one of the previous configurations, the display hub may include a data transmission port configured for selective wired connection to a remote unit.

In any one of the previous configurations, the display hub may include an internal hub frame securing the hypotube and first internal lumen to the display hub. In one configuration, the vascular occlusion catheter may further include an inflation hub in fluid communication with the display hub via an inflation shaft, the internal hub frame securing the inflation shaft and fluidly connecting the inflation hub with the first internal lumen.

One aspect of the present disclosure is directed to a vascular occlusion catheter for at least partial occlusion of a target vessel having an internal vessel wall. The vascular occlusion catheter includes an inflation hub having an inflation shaft extending therefrom; a proximal outer shaft; a distal outer shaft distally terminating with an atraumatic tip; and an occlusion balloon connected to the proximal outer shaft and the distal outer shaft. The proximal outer shaft has a first internal lumen and a second internal lumen, the first internal lumen being in fluid communication with the occlusion balloon. The distal outer shaft has a distal internal lumen. A hypotube has an internal hypotube lumen, the hypotube extending through the first internal lumen, through the occlusion balloon and into communication with the distal internal lumen. The hypotube operates as the primary load-bearing chassis of the vascular occlusion catheter. A first window is formed in the proximal outer shaft, and a proximal sensor is positioned within the second internal lumen facing the first window. A second window is formed in distal outer shaft, and a distal sensor is positioned within the distal internal lumen facing the second window. A display hub is positioned along the proximal outer shaft and has an internal hub frame, (i) the first internal lumen and the hypotube extend into the display hub and are secured to the internal hub frame, (ii) the inflation shaft extends into the display hub and is secured to the internal hub frame, the internal hub frame fluidly connecting the inflation hub with the first internal lumen, (iii) the second internal lumen extends into the display hub, the display hub being electrically connected with the proximal sensor via the second internal lumen, and (iv) the display hub is electrically connected with the distal sensor via the internal hypotube lumen and the distal internal lumen. The occlusion balloon, the proximal outer shaft and the distal outer shaft have a greatest outer diameter of seven French (7 Fr) or less in an uninflated condition.

In one configuration, the vascular occlusion catheter may further include a solid distal wire embedded in the distal outer shaft and extending toward the atraumatic tip, the solid distal wire tapering from a proximal end thereof to a distal end thereof. In one configuration, the solid distal wire may partially overlap, in a generally parallel arrangement, with the hypotube. In one configuration, the portion of the solid distal wire overlapping with the hypotube may be jacketed to the hypotube.

In one configuration, the display hub may include a data transmission port configured for selective wired connection to a remote unit.

BRIEF DESCRIPTION OF THE SEVERAL VIEWS OF THE DRAWINGS

The following description of embodiments of the disclosure will be better understood when read in conjunction with the appended drawings. It should be understood, however, that the disclosure is not limited to the precise arrangements and instrumentalities shown. In the drawings.

DETAILED DESCRIPTION OF THE DISCLOSURE

Figure 1A:
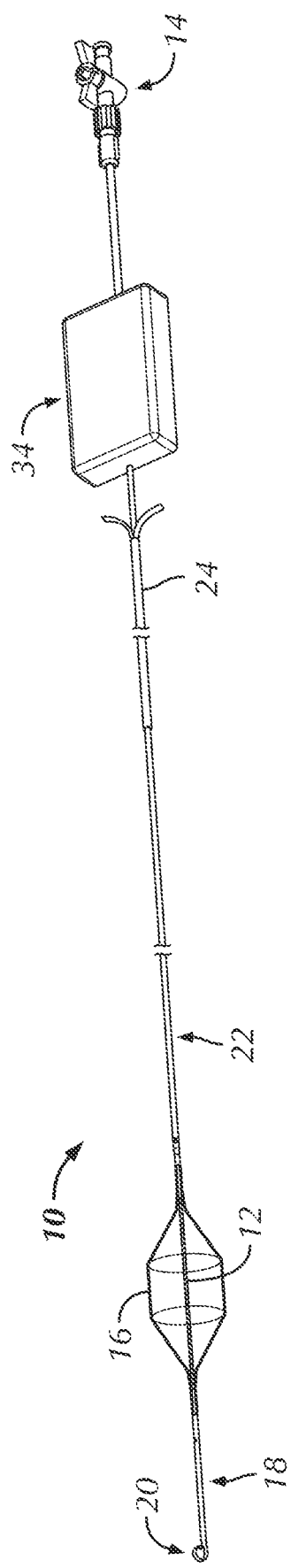
FIG. 1A is a perspective view of an occlusion catheter according to a first embodiment of the present disclosure.
Figure 1B:
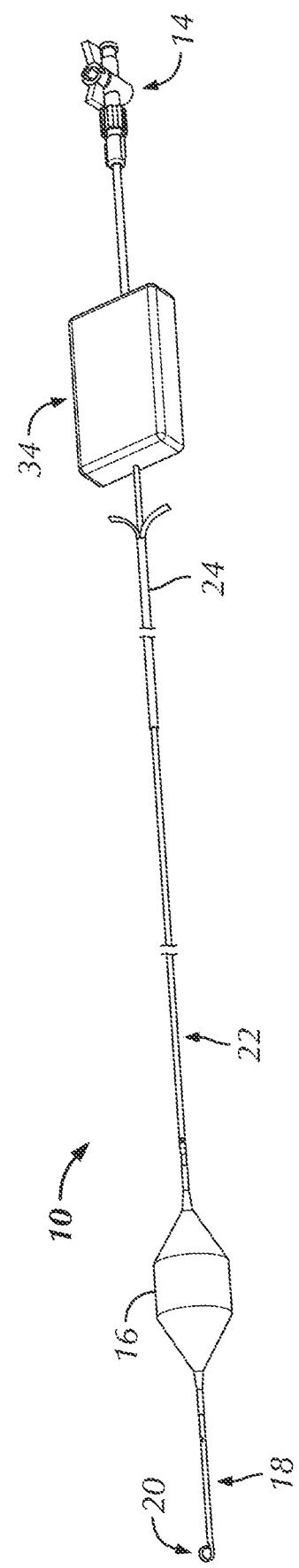
FIG. 1B is another perspective view of the occlusion catheter of FIG. 1A.
Figure 2A:
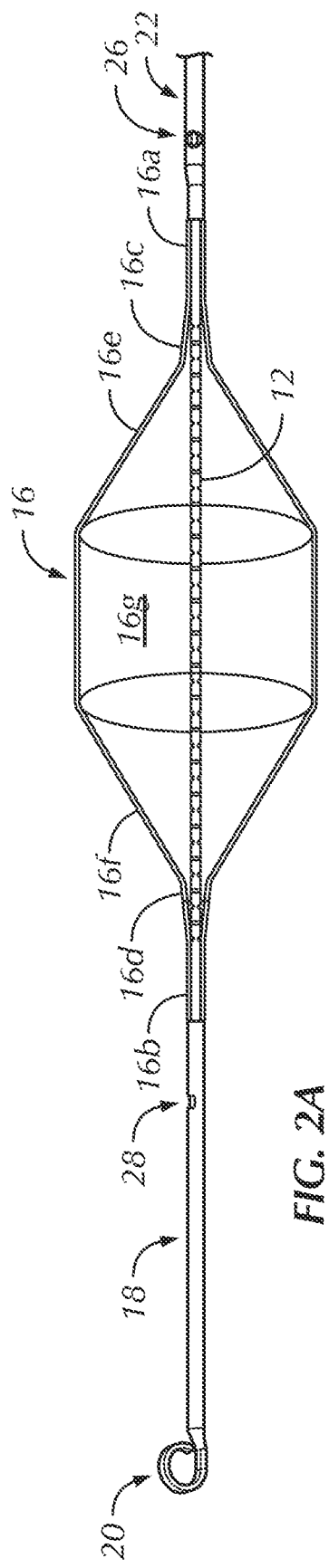
FIG. 2A is an expanded, partial perspective view of the occlusion catheter of FIG. 1A.
Figure 2B:
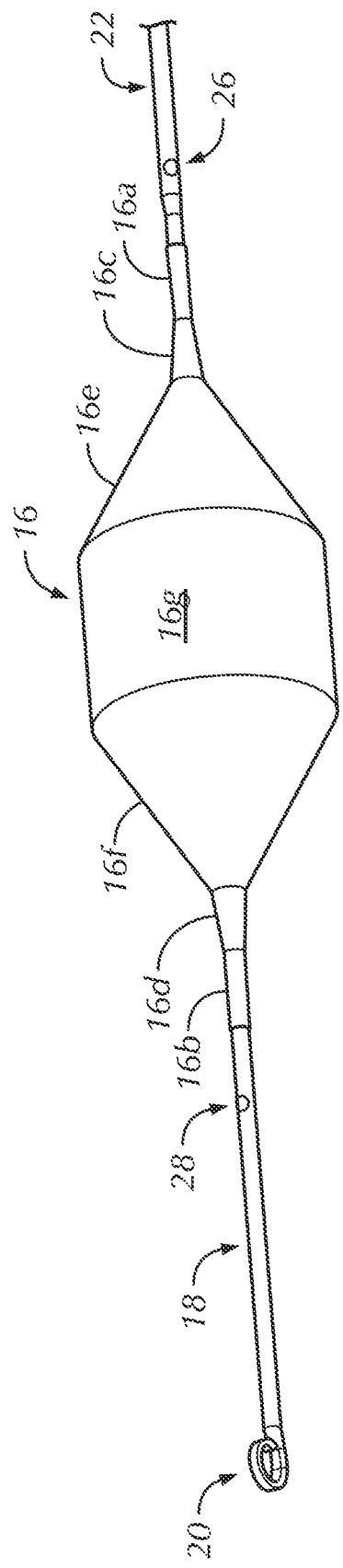
FIG. 2B is another expanded, partial perspective view of the occlusion catheter of FIG. 1A.
Figure 3A:
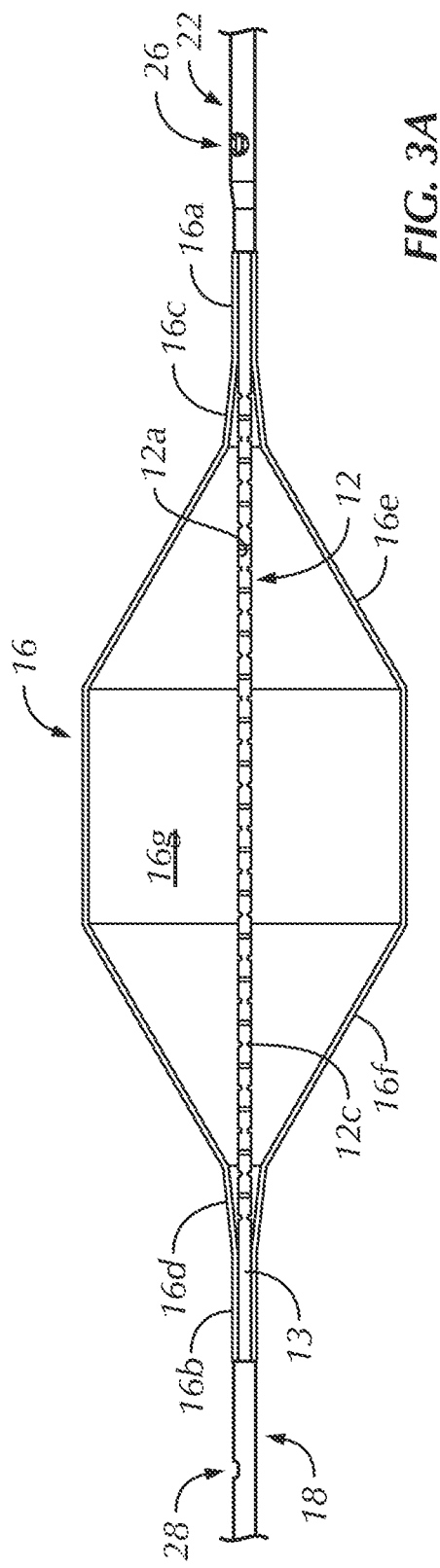
FIG. 3A is an expanded, partial elevational view of an occlusion balloon of the occlusion catheter of FIG. 1A.
Figure 3B:
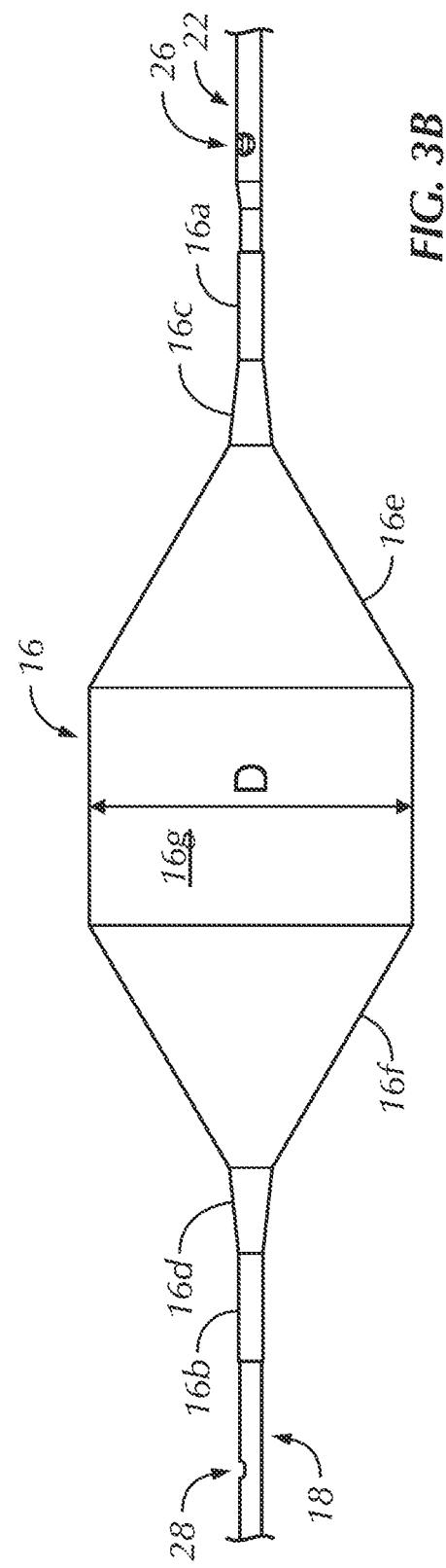
FIG. 3B is another expanded, partial elevational view of the occlusion balloon of the occlusion catheter of FIG. 1A.

Certain terminology is used in the following description for convenience only and is not limiting. The words "lower," "bottom," "upper" and "top" designate directions in the drawings to which reference is made. The words "inwardly," "outwardly," "upwardly" and "downwardly" refer to directions toward and away from, respectively, the geometric center of the occlusion catheter, and designated parts thereof, in accordance with the present disclosure. Unless specifically set forth herein, the terms "a," "an" and "the" are not limited to one element, but instead should be read as meaning "at least one." The terminology includes the words noted above, derivatives thereof and words of similar import.

It should also be understood that the terms "about," "approximately," "generally," "substantially" and like terms, used herein when referring to a dimension or characteristic of a component of the disclosure, indicate that the described dimension/characteristic is not a strict boundary or parameter and does not exclude minor variations therefrom that are functionally similar. At a minimum, such references that include a numerical parameter would include variations that, using mathematical and industrial principles accepted in the art (e.g., rounding, measurement or other systematic errors, manufacturing tolerances, etc.), would not vary the least significant digit.

Referring to the drawings in detail, wherein like numerals indicate like elements throughout, there is shown in FIGS. 1-25 an occlusion catheter, generally designated 10, in accordance with a first embodiment of the present disclosure. As shown, the catheter 10 includes a first shaft/hypotube 12. The hypotube 12 forms the structural backbone/chassis of the catheter 10. Stated differently, the hypotube 12 forms the primary load-bearing framework of the catheter 10, advantageously eliminating the necessity for a separate guidewire to provide such load bearing stability. The hypotube 12 may be constructed of a metal, a metal alloy, a polymer, a combination thereof, e.g., composite braided shafts, or the like. Non-limiting examples include stainless steel, nitinol, plastic reinforced with fiberglass, Kevlar® owned by E.I. Du Pont De Nemours and Company, and/or nylon. As will be described in further detail below, the hypotube 12 extends from an inflation hub 14 at a proximal end of the catheter 10 and terminates within or distally beyond an expandable occlusion balloon 16 of the catheter 10 (and proximate a distal end of the catheter 10).

The hypotube 12 defines an internal hypotube lumen 12a extending from a proximal end of the hypotube 12 and terminating within the occlusion balloon 16 (see, e.g., FIGS. 3A, 4-7). At a proximal end thereof, the hypotube lumen 12a is in fluid communication with the inflation hub 14. In one non-limiting example, the inflation hub 14 may take the form of a hub body 14a incorporating a combination stopcock and pressure relief valve 14b (see, e.g., FIGS. 11 and 12), such as described in International Patent Application Publication No. WO/2022/016109, titled "Inflation Hub for a Fluid Inflatable Apparatus", the entire contents of which are incorporated by reference herein. The combination stopcock and pressure relief valve 14b provides selective communication of the hypotube lumen 12a with an inflation device (not shown) while preventing overinflation of the expandable occlusion balloon 16 so that the balloon 16 does not burst inside a target vessel during a procedure. In another non-limiting example, the inflation hub 14 and the pressure relief valve 14b may take the form of the inflation hub and the pressure relief or pop-off valve described in International Patent Application Publication No. WO 2020/033372, titled "System and Method for Low Profile Occlusion Balloon Catheter" ("the '372 publication"), the entire contents of which are incorporated by reference herein. As should be understood by those of ordinary skill in the art, however, the presence of a pressure relief valve 14b is optional, depending on the construction of the occlusion balloon 16.

A solid distal wire 13 (FIGS. 3A, 4 and 5) extends from the terminal end of the hypotube lumen 12a toward a distal end of the catheter 10. In one configuration, the solid distal wire 13 may be welded, bonded or otherwise adjoined with the hypotube 12. In one configuration, the solid distal wire 13 may also be constructed of the same material as the hypotube 12 or may be constructed of another one of the suitable hypotube materials previously identified. A distal outer catheter shaft 18, e.g., a polymeric shaft, jackets at least a portion of the solid distal wire 13 and distally extends beyond the distal wire 13, terminating in an atraumatic tip or a P-tip 20, such as described in U.S. Pat. No. 10,569,062, titled "Low Profile Occlusion Catheter" ("the '062 patent"), the entire contents of which are incorporated by reference herein. In one configuration, the distal outer shaft 18 may be partially or fully bonded to the solid distal wire 13.

In one configuration, the expandable occlusion balloon 16 is sealingly mounted (in a manner understood, e.g., bonding, welding, a combination thereof or the like), at a proximal neck 16a thereof, directly to the hypotube 12 along a portion of the hypotube 12 having the internal hypotube lumen 12a. Optionally, a proximal outer catheter shaft 22, e.g., a polymeric shaft, jackets the hypotube 12 proximal to the occlusion balloon 16. The proximal neck 16a of the occlusion balloon 16 may additionally, or alternatively, be sealingly mounted to the proximal outer shaft 22. In one configuration, a distal neck 16b of the occlusion balloon 16 is sealingly mounted directly to the hypotube 12 along a portion of the hypotube 12 having the internal hypotube lumen 12a or along a portion of the solid distal wire 13. The distal neck 16b of the occlusion balloon 16 may additionally, or alternatively, be sealingly mounted to the distal outer shaft 18. In one configuration, any combination of the hypotube 12, the solid distal wire 13, the proximal outer shaft 22 and the distal outer shaft 18, may be radiopaque when viewed under radiographic imaging. For example, without limitation, the proximal outer shaft 22 and/or the distal outer shaft 18 may be impregnated with barium sulfate. Additionally, or alternatively, the hypotube 12 and/or the the solid distal wire 13 may be constructed of a radiopaque material, such as nitinol.

In one configuration, the expandable occlusion balloon 16 may take the form of a balloon as described in the '372 publication, the '062 patent, U.S. Pat. No. 10,149,962, titled "System and method for low-profile occlusion balloon catheter", U.S. Pat. No. 10,368,872, titled "System and method for low profile occlusion balloon catheter", or a combination thereof, the entire contents of each of which are incorporated by reference herein. The occlusion balloon 16 may be constructed of a semi-compliant or a substantially non-compliant material. Such balloon construction may benefit from a pressure-relief valve to avoid inadvertent balloon overinflation rupture. Alternatively, the occlusion balloon 16 may be constructed of a compliant material. Such balloon construction may not require a pressure-relief valve due to the expansion properties thereof. Although not so limited, a (substantially) non-compliant balloon 16 generally has growth of approximately two to approximately seven percent (2-7%) within the working range (balloon pressure) when inflated, a semi-compliant balloon 16 has growth of approximately seven to approximately twenty percent (7-20%) within the working range (balloon pressure) when inflated and a compliant balloon 16 has growth of approximately greater than twenty percent (20%±) within the working range (balloon pressure) when inflated, such as approximately one hundred to approximately three hundred percent (100%-300%) within the working range (balloon pressure) when inflated.

The occlusion balloon 16 may have a larger blown diameter D relative to the diameter of the destination/target vessel into which the occlusion balloon 16 will be inflated, e.g., an aorta. For example, the occlusion balloon 16 may have a blown diameter of approximately twenty-five to approximately thirty-five millimeters (~25-35 mm), that is configured to be approximately ten to approximately four hundred percent (10-400%) larger than the target vessel into which the occlusion balloon 16 is inserted and inflated for occlusion. The occlusion balloon 16 may, therefore, only be partially inflated when its outer surface comes into substantially full diametric contact with the internal surface of the target vessel. Accordingly, folds/creases (not shown) may remain at the outer surface of the balloon 16 along the axial length thereof. Such folds create channels (not shown) with the internal surfaces of the vessel or with other overlapping portions of the outer surface of the balloon 16 that allow partial perfusion or blood flow past the balloon 16 under the blood pressure within the vessel. The occlusion balloon 16 may also be further inflatable to substantially fill in the folds and achieve full occlusion of the vessel and prevent blood flow past the balloon 16. Alternatively, an occlusion balloon 16 having a smaller blown diameter (e.g., ~15 mm) and a greater working length, i.e., the length of the portion of the balloon 16 that contacts the target vessel, may be employed, which may also enable increased partial occlusion control of blood flow past the inflated balloon 16 under the blood pressure within the vessel. By increasing the balloon working length, the radial gap between the external balloon surface and blood vessel internal surface changes less per incremental balloon volume change. In turn, it becomes increasingly practicable for the operator to finetune partial occlusion, e.g., controlling the rate of blood flowing past the balloon relative to incremental balloon volume changes.

As previously described, the hypotube 12 extends through the occlusion balloon 16, and the occlusion balloon 16 overlaps with at least a portion of the hypotube 12 having the internal lumen 12a. As shown best in FIGS. 2A, 3A, 5 and 6, the hypotube 12 further includes a plurality of through holes/openings 12c in the sidewall thereof, e.g., laser cut, at least along a section of the hypotube 12 positioned within the occlusion balloon 16, thereby fluidly communicating the hypotube internal lumen 12a with an interior 16g of the occlusion balloon 16. Thus, the hypotube internal lumen 12a fluidly communicates the inflation hub 14 with the interior 16g of the occlusion balloon 16 and operates as a balloon inflation lumen with the openings 12c forming balloon inflation ports, such that the occlusion balloon 16 is inflatable via the hypotube internal lumen 12a and the openings 12c.

Figure 31:
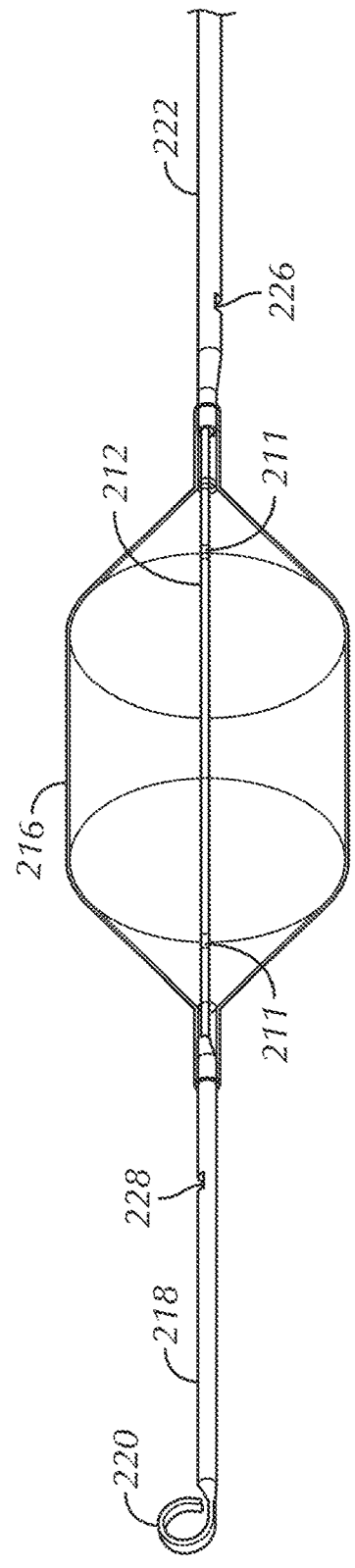
FIG. 31 is an expanded, partial perspective view of the occlusion catheter of FIG. 30.

As previously described, the hypotube 12 provides sufficient structural integrity, e.g., column strength, to safely support balloon inflation within the target vessel without collapse. As should be understood, the diameter of the hypotube internal lumen 12a as well as the number of openings 12c are selected to provide a sufficient balloon inflation rate. The openings 12c also provide a reduced stiffness of the hypotube 12 generally in the area of the occlusion balloon 16 to facilitate insertion of the occlusion catheter 10 into the patient's vessel, which may be along a curved and tortuous path. Additionally, the regionally reduced stiffness generally in the area of the occlusion balloon 16 (in combination with the tapered distal wire 13 as described below) assists to achieve a more gradual stiffness transition from the stiffest region of the occlusion catheter 10, i.e., the proximal outer shaft 22, to the atraumatic tip 20. Advantageously, the openings 12c may also show up when using radiographic imaging to provide the user with balloon placement information, occlusion length, and the like. Accordingly, the openings 12c may supplement or replace the radiopaque platinum iridium marker bands (see e.g., FIG. 31—marker bands 211) positioned upon the hypotube 12 within the occlusion balloon 16, which roughly indicate the balloon 'shoulders', e.g., the bounds of the inflated balloon 16 that contact the target vessel wall.

Figure 4:
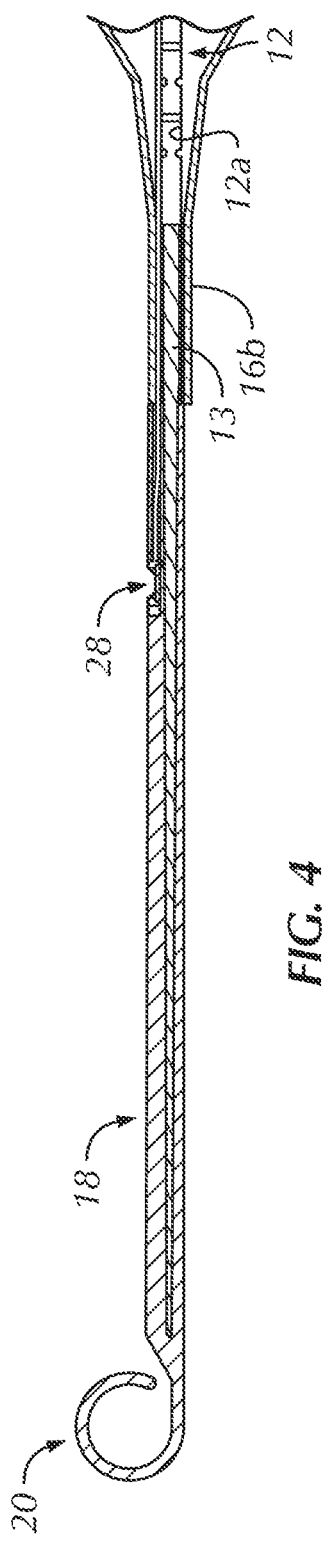
FIG. 4 is an expanded, partial cross-sectional view of a distal section of the occlusion catheter of FIG. 1A.
Figure 5:
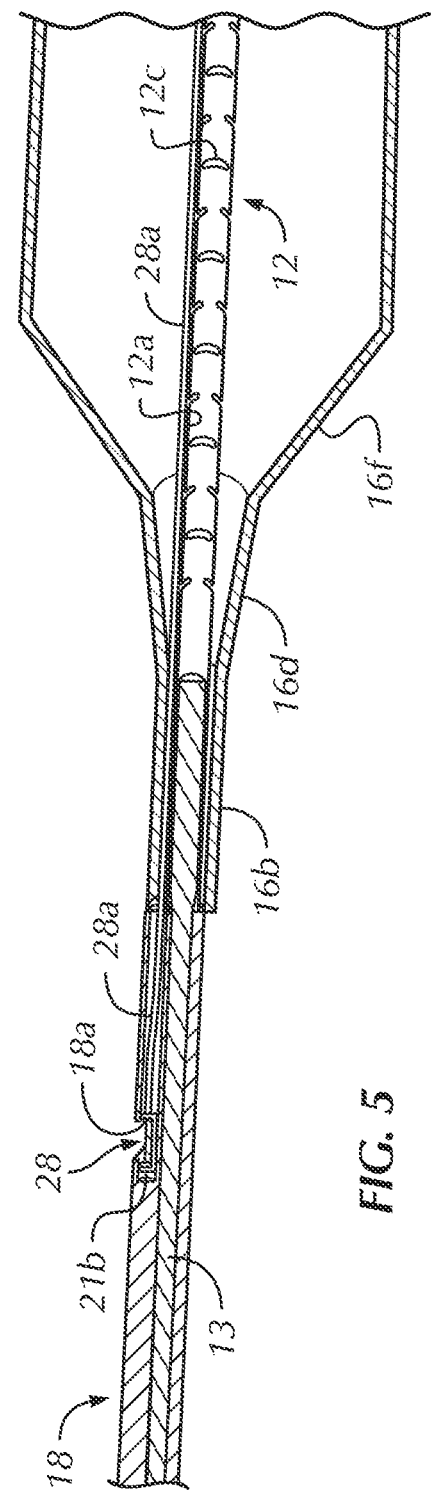
FIG. 5 is a further expanded, partial cross-sectional view of a distal section of the occlusion catheter of FIG. 1A.
Figure 6:
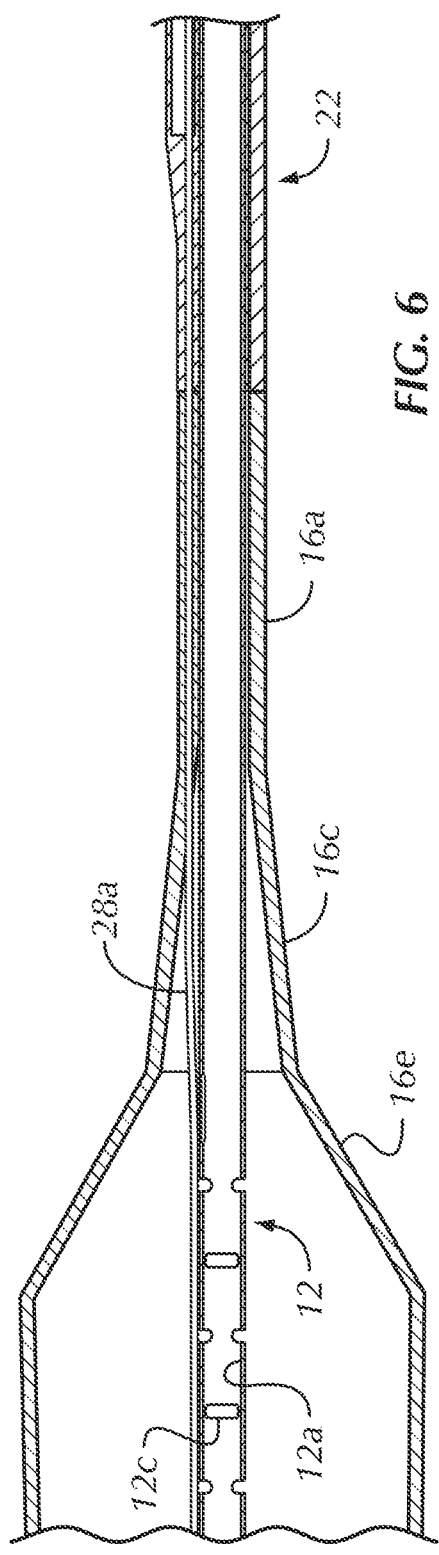
FIG. 6 is an expanded, partial cross-sectional view of a proximal section of the occlusion catheter of FIG. 1A.

As shown best in FIGS. 4 and 5, the solid distal wire 13 preferably tapers from a proximal end thereof (adjoining the terminal end of the hypotube 12) to the distal end thereof (proximate a base of the atraumatic tip 20). Advantageously, such tapering provides a progressively, distally decreasing transition in stiffness of the catheter 10 from the terminal end of the hypotube 12 to the atraumatic tip 20, equipping the distal end of the catheter 10 with increased maneuverability and steerability. Advantageously, the openings 12c within the occlusion balloon 16 also contribute to reducing bending stiffness of the catheter 10 along the hypotube 12. Thus, the number and location of the openings 12c may be determined to enable adequate balloon inflation as well as to provide, in combination with the tapered solid distal wire 13, a progressive/gradual bending stiffness transition, i.e., decrease, from the proximal outer shaft 22 to the atraumatic tip 20. For example, the requisite diameter of the hypotube 12 to support an appropriate balloon inflation rate, in combination with the hypotube 12 construction, may result in a stiffer hypotube 12 than desired for insertion of the occlusion catheter 10 into the patient's vasculature. Accordingly, the openings 12c may be employed up to along the entire length of the hypotube 12 to counteract the increased stiffness of the hypotube 12.

As should be understood by those of ordinary skill in the art, an insertion cannula or sheath (not shown) is employed for introducing the occlusion catheter 10 into a patient and remains in the access site for retraction and/or exchange of the occlusion catheter 10. Therefore, a greatest outer diameter of the catheter 10 should be small enough for insertion into the insertion sheath. A seven French (7 Fr) or smaller insertion sheath typically results in the access site through the patient's skin and into the target vessel being re-closed by holding manual pressure for a period of time, such as twenty to thirty minutes (20-30 min). If the insertion sheath has an inner diameter greater than seven French (7 Fr), surgical repair of the access site may be required, thereby further complicating a procedure. Accordingly, it is significant for a greatest outer diameter of the catheter 10 (with the balloon 16 uninflated/folded) to be seven French (7 Fr) or smaller, e.g., six French (6 Fr), five French (5 Fr) or four French (4 Fr), to enable sliding through a seven French (7 Fr) or smaller insertion sheath and minimize the need for access site surgical repair. Thus, the outer diameter of the proximal outer shaft 22, the proximal and distal necks 16a, 16b of the occlusion balloon 16 as well as the central body of the occlusion balloon 16, and the distal outer shaft 18 are each seven French (7 Fr) or smaller.

Also, to that end, the openings 12c of the hypotube 12 within the occlusion balloon 16, in combination with the hypotube material, e.g., an elastic material such a nitinol, also enables the occlusion balloon to be mounted to the hypotube 12 (or as otherwise previously described) in a relatively taut manner, such that the uninflated/folded balloon 16 is also seven French (7 Fr) or smaller. That is, conventionally, slight slack is required in an occlusion balloon in the uninflated state to account for tensioning of the balloon surface upon inflation. Otherwise increased tensile forces at the proximal and distal necks of the balloon upon inflation may result in catastrophic damage to the bond between the balloon and the catheter. Such slack in the uninflated/folded occlusion balloon may thicken portions of the uninflated/folded occlusion balloon to greater than seven French (7 Fr). Conversely, the openings 12c of the hypotube 12 within the occlusion balloon 16, in combination with the hypotube material, increase the bendability/deflectabilty of the hypotube 12. Accordingly, upon inflation of the relatively taut/stretched occlusion balloon 16, resulting in a decrease in the distance between the proximal and distal necks 16a, 16b thereof, the hypotube 12 elastically bends/bows in response, thereby accommodating the decrease in distance between proximal and distal necks 16a, 16b without causing damage to the respective bonds between the between proximal and distal necks 16a, 16b and the hypotube 12. Upon subsequent deflation of the occlusion balloon 16, stored elastic energy in the curved/bowed hypotube 12 substantially straightens the hypotube 12 back out and re-stretches the occlusion balloon 16 in the uninflated state. Advantageously, therefore, mounting of the uninflated occlusion balloon 16 to the hypotube 12 in a relatively taut manner assists in decreasing the outer profile of the folded occlusion balloon 16 to seven French (7 Fr) or smaller.

A peel-away sheath 24 (shown best in FIGS. 1A, 1B and 9) is pre-positioned over the occlusion balloon 16 in the folded state/configuration to maintain the folded configuration thereof prior to use. The peel-away sheath 24 assists to retain the occlusion balloon 16 at a diameter of seven French (7 Fr) (2.3 mm) or less. The peel-away sheath 24 may additionally be employed to straighten the atraumatic tip 20 for entry into the insertion sheath.

As shown best in FIGS. 3A, 3B, and 5-7, the inflated/blown occlusion balloon 16 may define a dual tapered conical shape adjacent the proximal and distal necks 16a, 16b thereof, respectively. That is, each of the terminal ends of the occlusion balloon 16 includes a respective neck 16a, 16b bonded, or otherwise mounted, to the hypotube 12 (or as otherwise previously described), leading to a first, shallow, radially outwardly angled section 16c, 16d, respectively, and followed by a second, more acutely radially outwardly angled section 16e, 16f, respectively, extending to the outer, blown diameter D of the occlusion balloon 16. In one non-limiting configuration, the first, shallow, radially outwardly angled section(s) 16c, 16d may define an incline angle of between approximately 3° and approximately 20°, such as, for example, approximately 5° or approximately 6°. In one non-limiting configuration, the second, more acutely radially outwardly angled section(s) 16e, 16f may define an incline angle of between approximately 10° and approximately 45°, such as, for example, between approximately 25° and approximately 30°.

Figure 23:
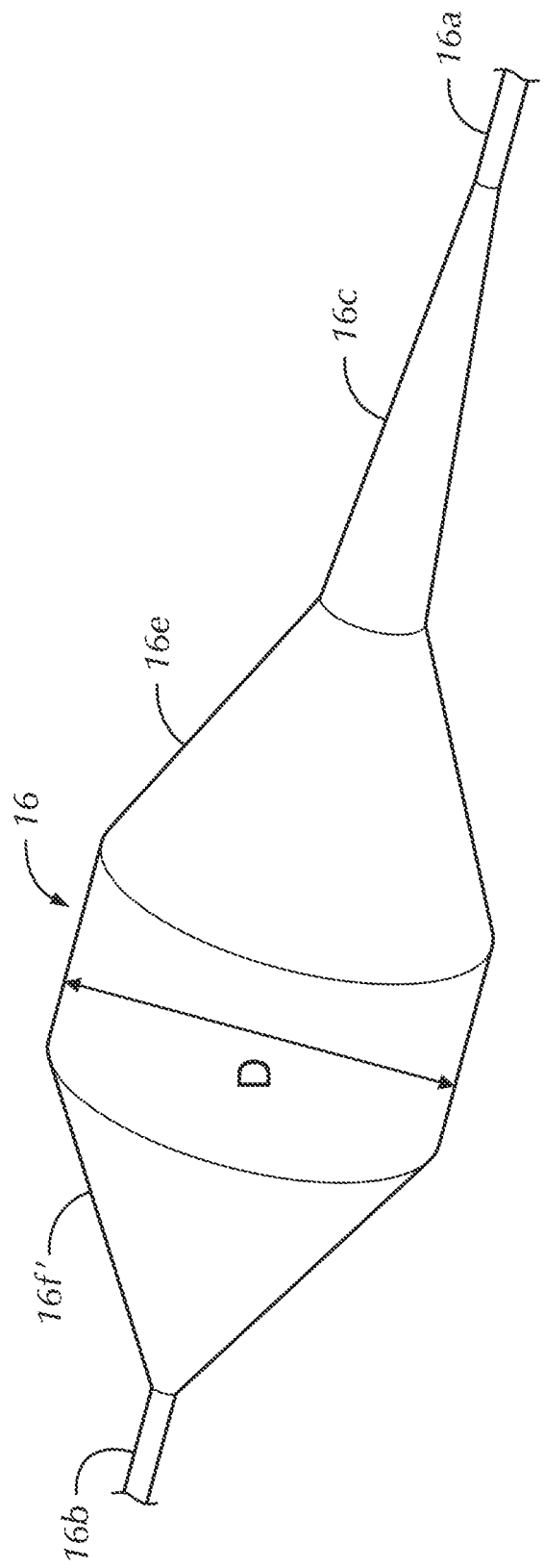
FIG. 23 is an expanded, partial perspective view of an alternative configuration of the occlusion balloon of the occlusion catheter of FIG. 1A.

Alternatively, the inflated/blown occlusion balloon 16 may include one end having a dual tapered conical shape and the opposing end having a single tapered conical shape. For example, as shown in FIG. 23, the proximal end of the occlusion balloon 16 includes a proximal neck 16a, leading to an extended first, shallow, radially outwardly angled section 16c, followed by a second, more acutely radially outwardly angled section 16e extending to the outer, blown diameter D of the occlusion balloon 16. Conversely, the distal end of the occlusion balloon 16 includes a distal neck 16b leading to a single, more acutely radially outwardly angled section 16f extending to the outer, blown diameter D of the occlusion balloon 16.

Advantageously, the more peripherally located first, shallow, radially outwardly angled section(s) 16c, 16d facilitate recapture of the uninflated/folded occlusion balloon 16 into the insertion sheath, whereas the adjoining, second, more acutely radially outwardly angled sections 16e, 16f more rapidly lead the exterior profile of the occlusion balloon 16 to the blown diameter D thereof. Maximizing the body portion of the occlusion balloon periphery that defines the blown diameter D thereof, and, in turn, the portion of the occlusion balloon periphery that contacts the target vessel internal wall, is advantageous for enhancing vessel occlusion properties. As should be understood by those of ordinary skill in the art, the occlusion balloon 16 may alternatively define more differently tapered conical sections than the dual tapered conical shape, and/or, as previously described, may define differing proximal and distal sides.

Figure 24A:
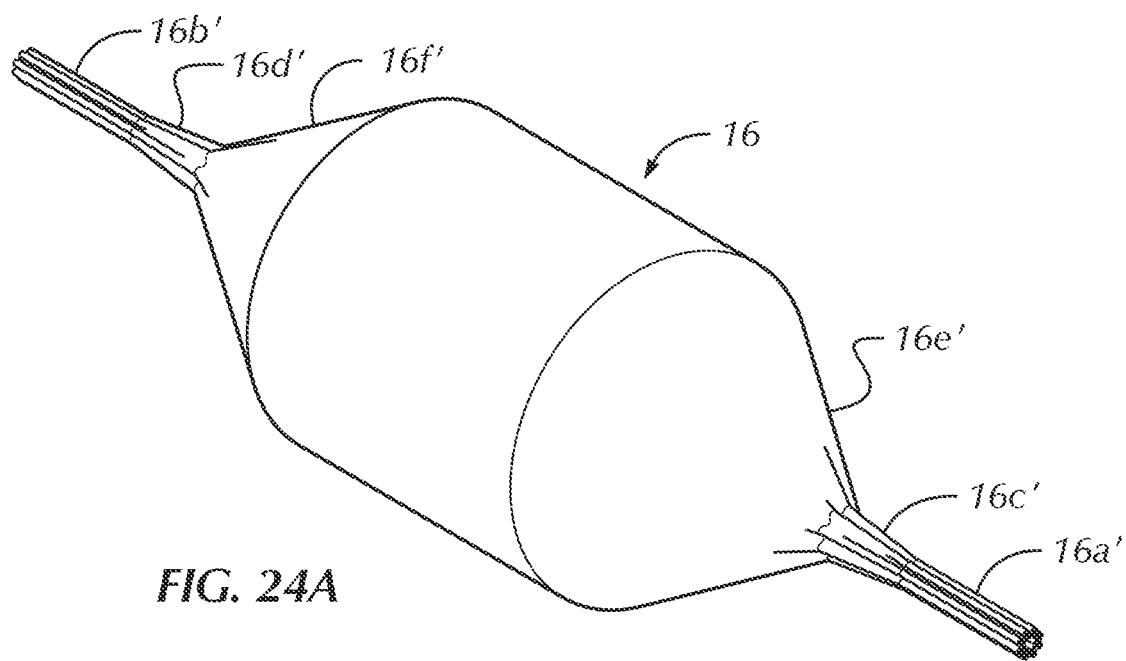
FIG. 24A is an expanded, partial perspective view of another alternative configuration of the occlusion balloon of the occlusion catheter of FIG. 1A.
Figure 24B:
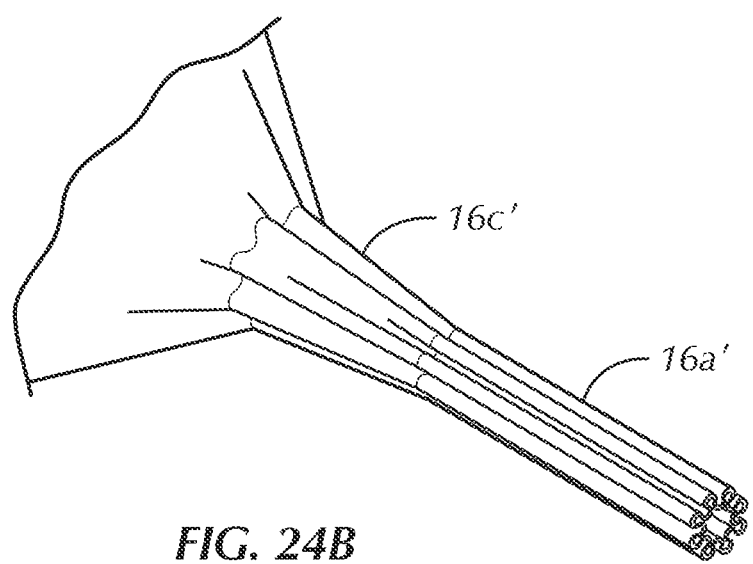
FIG. 24B is a further expanded and further partial perspective view of the occlusion balloon of FIG. 24A.
Figure 25:
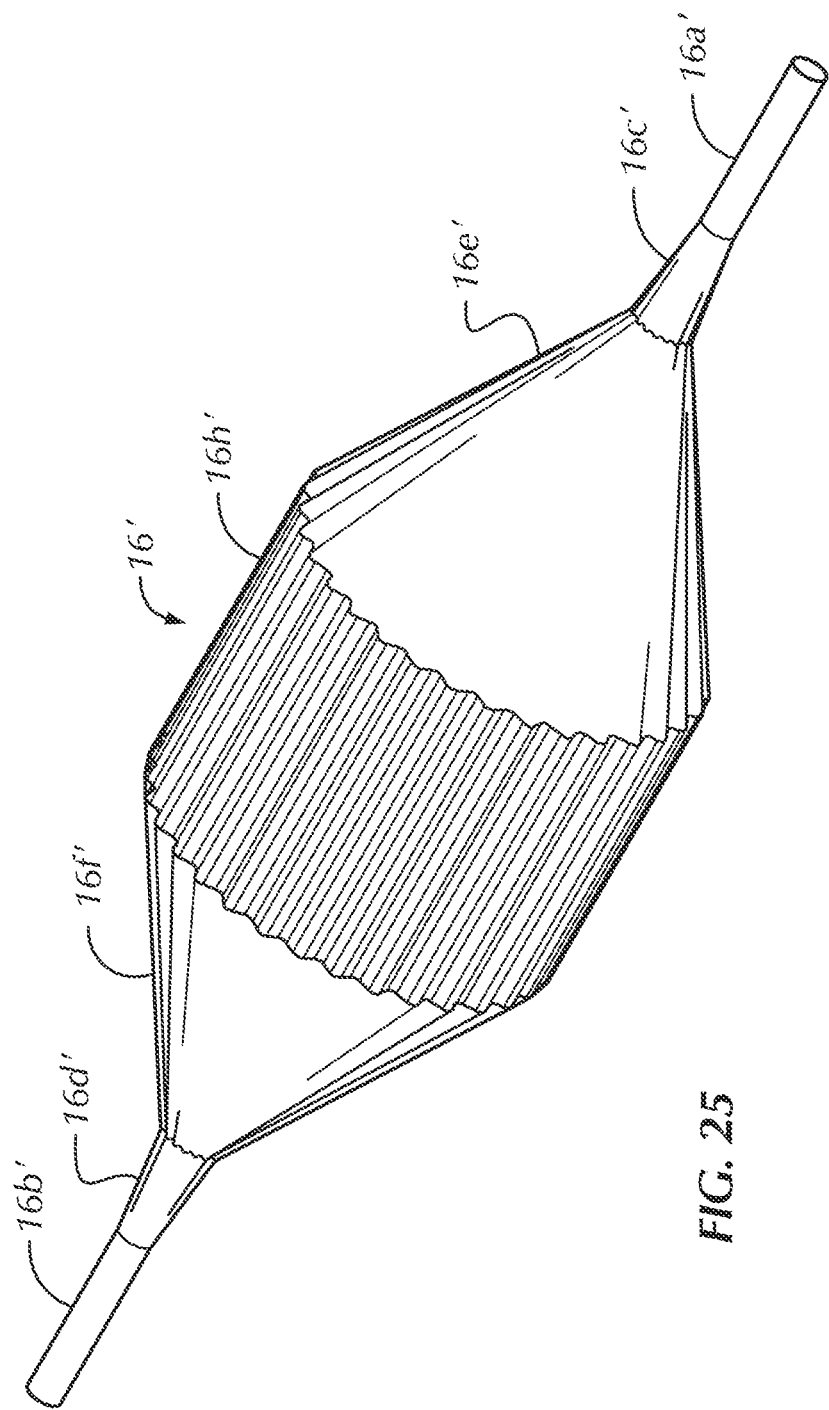
FIG. 25 is a partial perspective view of another alternative configuration of the occlusion balloon of the occlusion catheter of FIG. 1A.

In one configuration, as shown in FIGS. 24A, 24B, the occlusion balloon 16 may be constructed of folded/channeled balloon material along the proximal and distal necks 16a', 16b'. Additionally, or alternatively, at least one of the first, shallow, radially outwardly angled sections 16c', 16d', may be constructed of folded\channeled balloon material. In another configuration, as shown in FIG. 25, the conical sections, 16c', 16d'. 16e', 16f and/or the central body 16h' of the occlusion balloon 16' defining the maximum diameter may be constructed of folded\channeled balloon material. Advantageously, the folds form and maintain creases in the balloon material to assist balloon material collapse in a more predictable and compact manner. Recapture of the balloon material in a predictable and compact manner assists with balloon deflation and passing through the low-profile insertion sheath.

In some configurations, the occlusion catheter 10 may also include a proximal sensor 26 and/or a distal sensor 28. In the illustrated embodiment, as shown best in FIGS. 2A-7, the proximal sensor 26 is positioned proximally of the occlusion balloon 16 and the distal sensor 28 is positioned distally of the occlusion balloon 16. In one configuration, one or both of the proximal and distal sensors 26, 28 may take the form of Micro Electro-Mechanical System ("MEMS") sensors, but the disclosure is not so limited. In one configuration, one or both of the proximal and distal sensors 26, 28 may be pressure sensors. As should be understood, data from the distal pressure sensor 28, positioned upstream of the occlusion balloon 16 with respect to blood flow when in use, is preferably configured to indicate whether sufficient blood flow is reaching vital organs such as the brain and/or heart of the patient to keep the patient alive. The proximal pressure sensor 26, positioned downstream of the occlusion balloon 16 with respect to blood flow when in use, is preferably configured to indicate the level of occlusion of the target vessel attained and, in turn, (in the case of partial occlusion) the blood flow to organs and tissue below the occlusion location. When placed in the aorta, for example, the proximal and distal pressure sensors 26, 28 directly measure central aortic pressure downstream and upstream of the occlusion balloon 16, respectively. Direct and unimpeded measurement of central aortic pressure is advantageous due to the accuracy and immediacy of the measurement.

Additionally, or alternatively, the occlusion catheter 10 may include a pressure sensor 27 (shown schematically in FIG. 8) within the occlusion balloon 16 to measure intra-balloon pressure. Wiring for the pressure sensor 27 may be similar to wiring for the distal sensor 28, e.g., along and/or within the hypotube 12, as will be described in further detail below. As should be understood, intra-balloon pressure may be measured anywhere along the balloon inflation lumen, and, therefore, the pressure sensor 27 is not limited to positioning within the occlusion balloon 16. Rather, the pressure sensor 27 may be fluidly connected with the balloon inflation lumen anywhere from the balloon 16 and proximal thereto. As also should be understood, the catheter 10 may additionally, or alternatively, include one or more flow sensors, temperature sensors, pH sensors, lactate sensors, ion sensors, a combination thereof or the like to indicate other physiological parameters, that may be mounted to the occlusion catheter 10 above or below the occlusion balloon 16.

Figure 7:
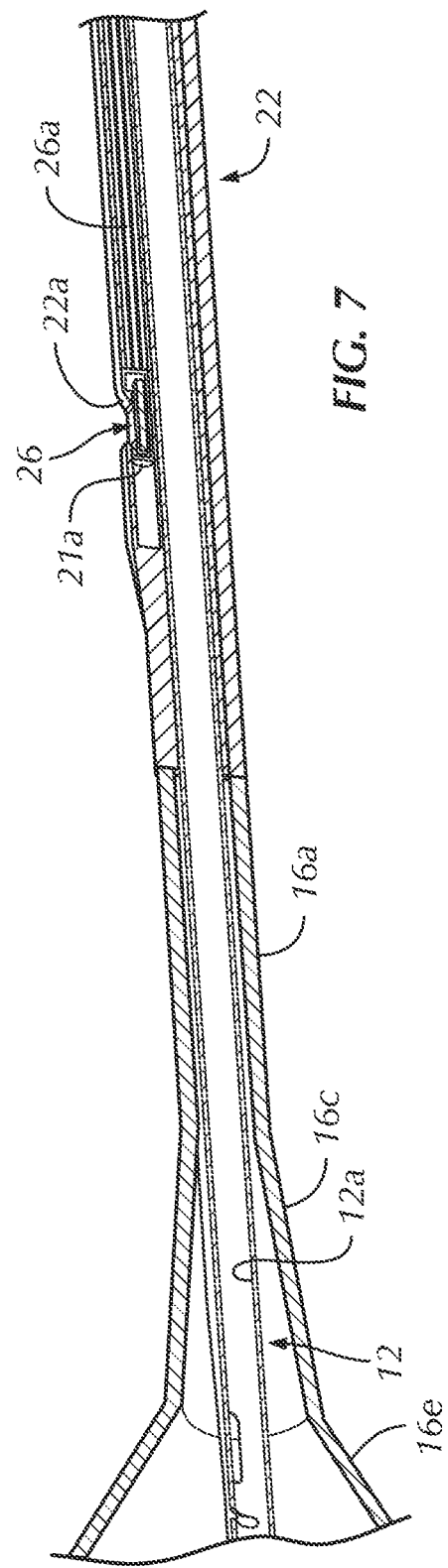
FIG. 7 is a further expanded, partial cross-sectional view of a proximal section of the occlusion catheter of FIG. 1A.
Figure 8:
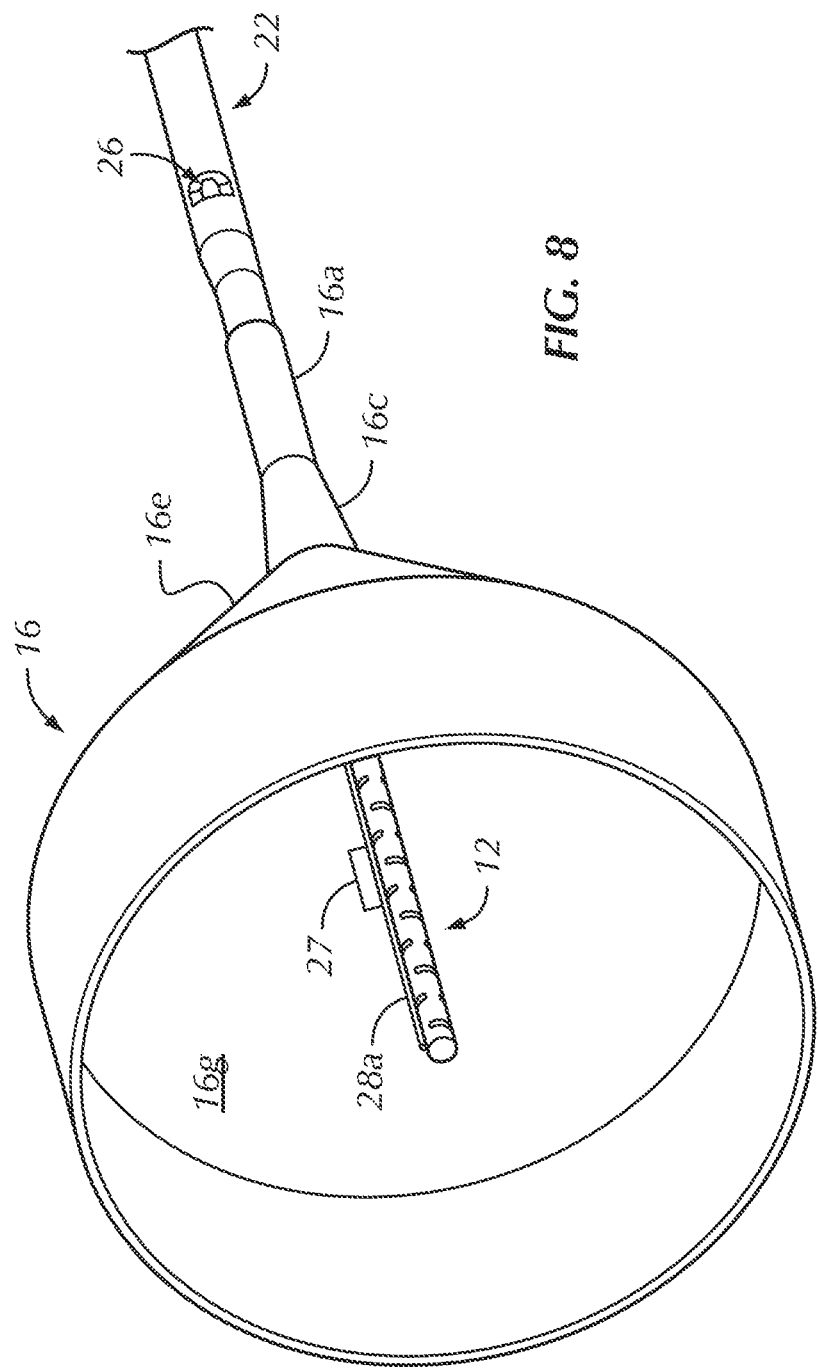
FIG. 8 is a perspective, cross-sectional view of the occlusion catheter of FIG. 1A, taken through the occlusion balloon.

As shown best in FIG. 7, the proximal MEMS sensor 26 is embedded in a window/opening 22a formed in the sidewall of the proximal outer shaft 22. The proximal sensor 26 is suspended in a first, generally tubular sensor case 21a sealingly mounted in the proximal outer shaft 22 and facing the window 22a. Similarly, and as shown best in FIGS. 4 and 5, the distal MEMS sensor 28 is embedded in a window/opening 18a formed in the sidewall of the distal outer shaft 18. The distal sensor 28 is also suspended in a second, generally tubular sensor case 21b sealingly mounted in the distal outer shaft 18 and facing the window 18a. The windows 22a, 18a provide access for direct fluid, e.g., blood, contact with the MEMS sensors 26, 28, respectively, for pressure measurements. Advantageously, the MEMS sensors 26, 28 are sized to be employed without increasing the maximum catheter 10 diameter of seven French (7 Fr) or smaller.

In one configuration, where the proximal and distal sensors 26, 28 (and/or sensor 27 if employed) are pressure sensors, one or both of the proximal and distal sensors 26, 28 may take the form of an absolute sensor. Accordingly, as described below with respect to FIG. 17, a barometric pressure transducer may be employed to convert absolute pressure data to gauge-based pressure data. Conversely, one or both of the proximal and distal sensors 26, 28 (and/or sensor 27 if employed) may take the form of a gauge sensor. In such form, the gauge sensor(s) may be vented to the atmosphere via a lumen, such as, for example, without limitation, via one of the various lumens described herein, in order to provide the sensor itself with an atmospheric pressure reference.

Figure 9A:
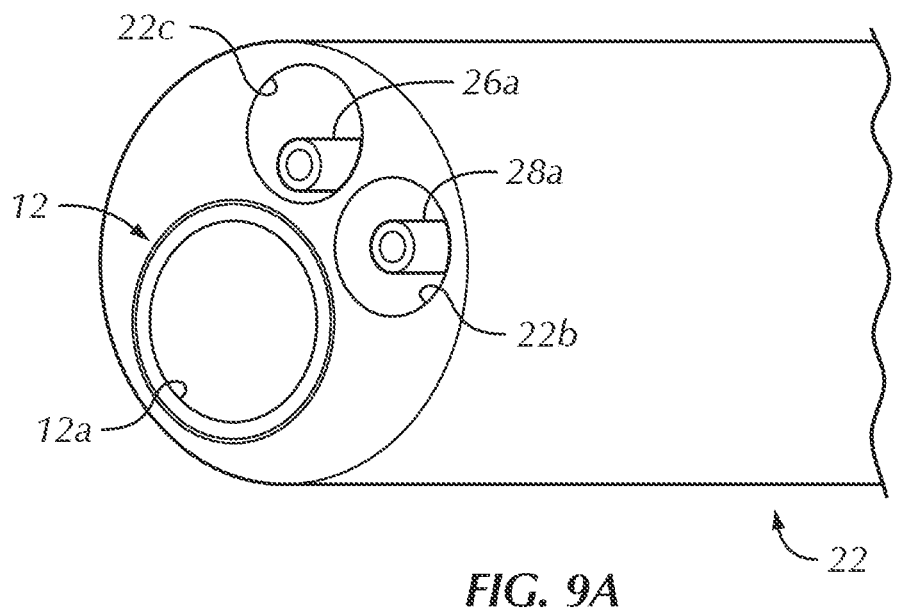
FIG. 9A is a perspective, cross-sectional view of the occlusion catheter of FIG. 1A, taken through a proximal catheter shaft of the occlusion catheter.
Figure 9B:
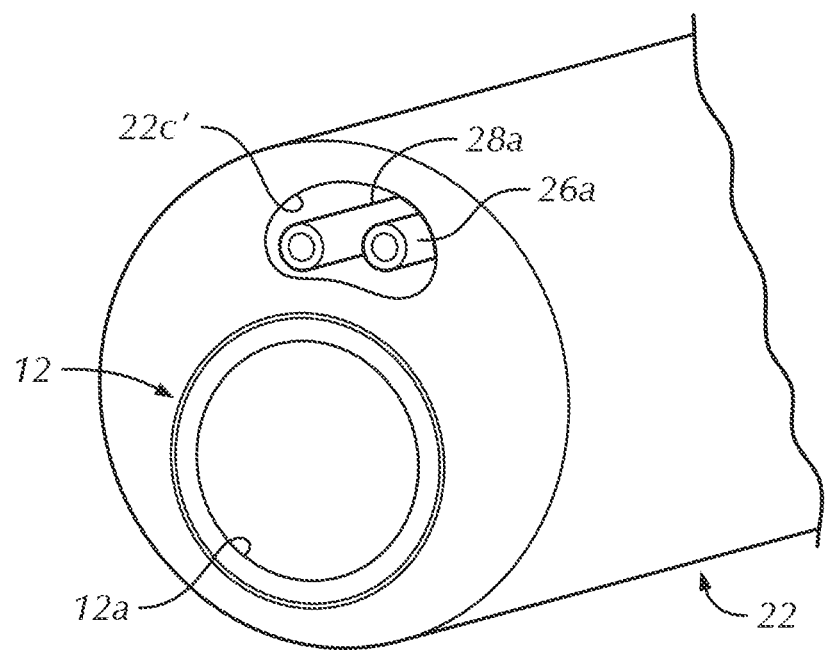
FIG. 9B is a perspective, cross-sectional view of the occlusion catheter of FIG. 1A, taken through an alternatively configured proximal catheter shaft of the occlusion catheter.

As shown best in FIGS. 4-9b, the wiring 28a of the distal sensor 28 is routed proximally from the distal sensor 28 through the distal outer shaft 18 to the hypotube 12, and travels substantially along the hypotube 12 (e.g., within the occlusion balloon 16) (see FIG. 8) and then into and through the proximal outer shaft 22. For example, the distal sensor signal wire 28a may be routed upon an external periphery of the hypotube 12, particularly within the occlusion balloon 16. Alternatively, at least a section of the distal sensor signal wire 28a may be routed into the hypotube internal lumen 12a, e.g., via an entry port and an exit port in the hypotube 12. The proximal sensor 26 also includes a proximal sensor signal wire 26a extending proximally therefrom. As shown in FIG. 9a, in addition to jacketing the hypotube 12, the proximal catheter shaft 22 may also include additional internal lumens 22b, 22c, for travel of the sensor signal wires 28a, 26a, therethrough, respectively. The internal lumens 22b, 22c may be dimensioned to fit the sensors 26, 28 themselves therein, to assist with assembly of the catheter 10. As should be understood, however, the internal lumens 22b, 22c, may be dimensioned in a smaller size in order to accommodate additional lumens, and/or a larger hypotube 12. Alternatively, as shown in FIG. 9b, the sensor signal wires 28a, 26a may travel through a single lumen 22c' in the proximal catheter shaft 22, or, one or both of the sensor signal wires 28a, 26a may be jacketed to the hypotube 12, e.g., via a shrink tube, within the proximal catheter shaft 22.

Figure 10A:
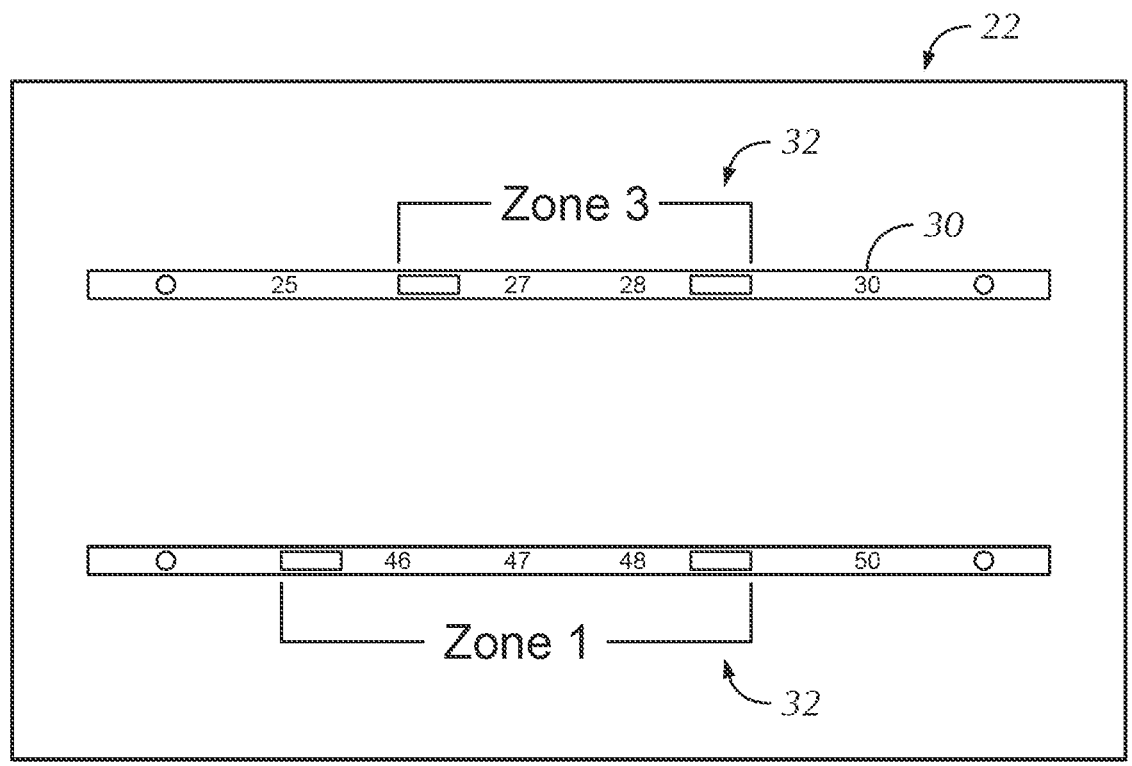
FIG. 10A is a schematic view of depth markings on an external surface of the proximal catheter shaft of the occlusion catheter of FIG. 1A.
Figure 10B:
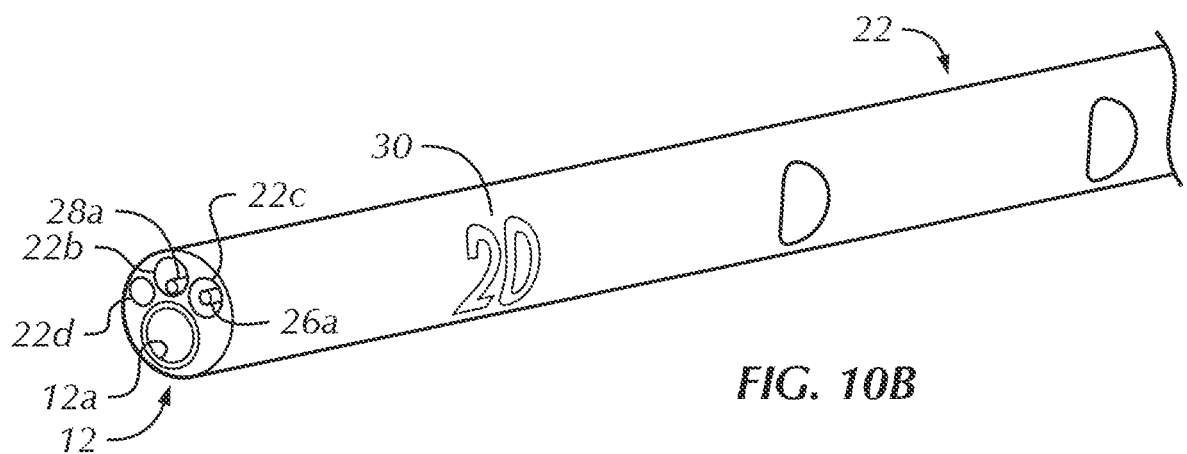
FIG. 10B is an expanded, partial perspective view of an alternative configuration of the proximal catheter shaft of the occlusion catheter of FIG. 1A.
Figure 11:
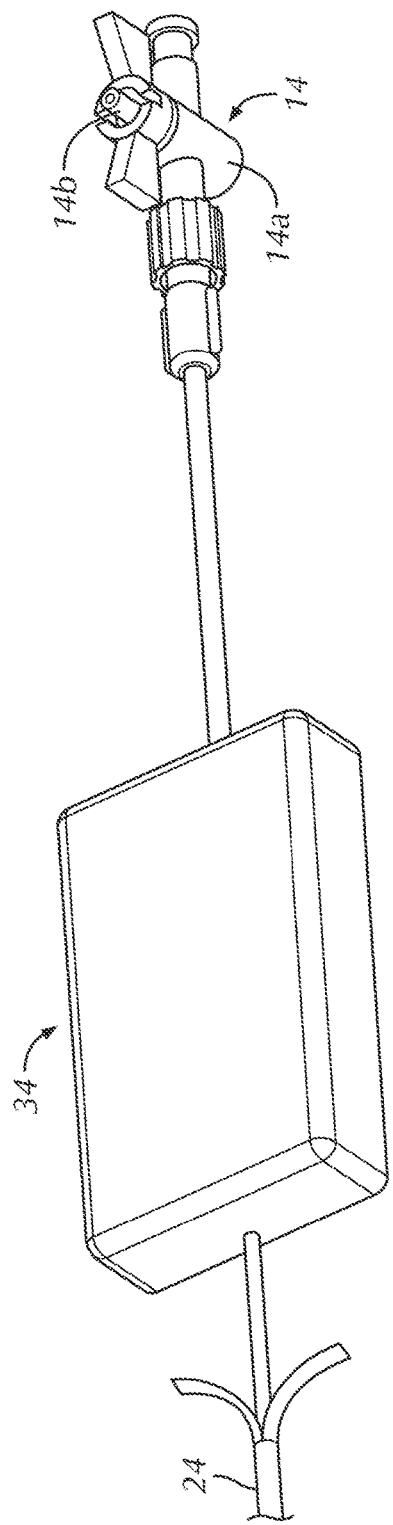
FIG. 11 is an expanded, partial perspective view of a proximal portion of the occlusion catheter of FIG. 1A, including a display hub thereof.
Figure 12:
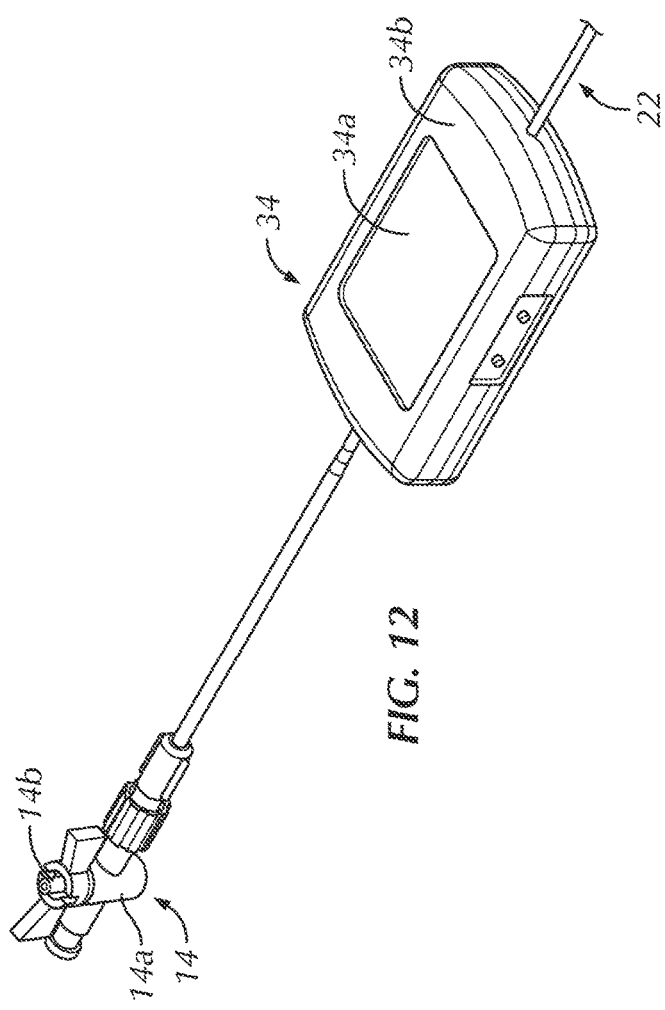
FIG. 12 is another expanded, partial perspective view of the proximal portion of the occlusion catheter of FIG. 1A, including the display hub thereof.

The proximal shaft 22 may include additional lumens, such as an additional lumen 22d shown in FIG. 10B, receiving additional sensor signal wire(s) therethrough. In one configuration, the additional lumen 22d may additionally, or alternatively, serve as a guidewire lumen, for optional use of a guidewire (not shown) with the occlusion catheter 10 in a manner practiced in the art for introducing the occlusion catheter 10 or another catheter into the patient's vessel. In such a configuration, the occlusion catheter 10 may include a guidewire exit port (not shown) proximate a proximal end of the occlusion balloon 16. Alternatively, a guidewire exit port may be positioned distally of the occlusion balloon 16, such as at a base of the atraumatic tip 20.

As shown in FIGS. 10A, 10B at least the proximal outer shaft 22 may include depth markings 30 on an external surface thereof that assist a user in properly placing the occlusion catheter 10 during use by indicating the depth of insertion, as indicated by the depth markings 30. Additionally, or alternatively, the depth markings 30 may include zone markings 32, such as zone I, zone II, and zone III representing locations in the patient's vessel, e.g., the aorta, wherein the occlusion balloon 16 is likely positioned during use. For example, the target location of the occlusion balloon 16 in zone I generally extends from the origin of the left subclavian artery to the coeliac artery, zone II generally extends from the coeliac artery to the most caudal renal artery and zone III generally extends distally from the most caudal renal artery to the aortic bifurcation.

Turning to FIGS. 1A, 1B and 11-16, the occlusion catheter 10 may further include a display hub 34 positioned along the proximal outer catheter 22, between the proximal sensor 26 and the inflation hub 14. The display hub 34 includes a display screen 34a configured to display key parameters, such as, without limitation, real-time central aortic pressure data from the pressure sensors 26, 28, as well as intra-balloon pressure data from sensor 27. Such parameters may be displayed numerically, via waveforms or both. As should be understood, the screen 34a may display additional parameters, such as, but not limited to, data from other sensors employed in the occlusion catheter 10 (such as previously described), full or partial occlusion indication, an occlusion duration timer, blood flow rate, battery life, a combination thereof or the like. Data from other sensors may include temperature, balloon volume, pH level, lactate level, pulse oxygenation, bicarbonate level, arterial blood gas level and the like. The display hub 34 may also be equipped and configured to provide alerts to the practitioner, e.g., visual and/or audible, related to the displayed information.

Figure 13:
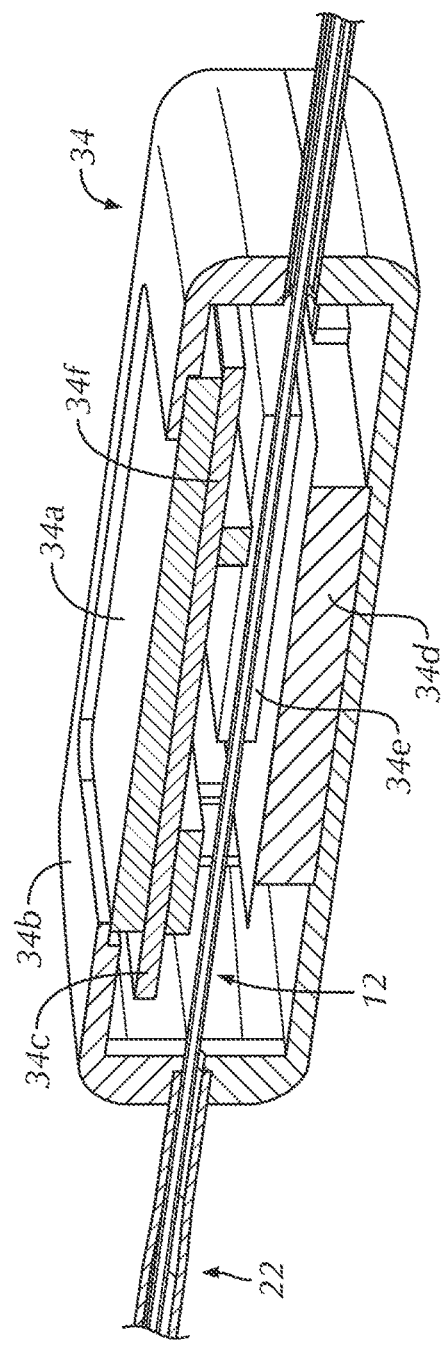
FIG. 13 is a further expanded, partial cross-sectional view of the display hub of the occlusion catheter of FIG. 1A.
Figure 14:
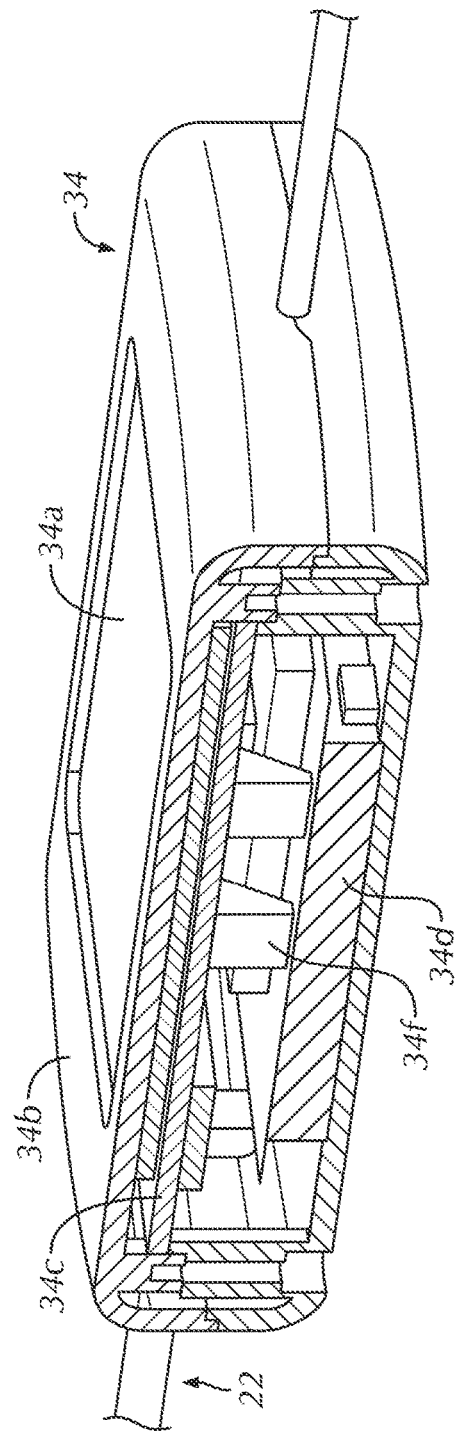
FIG. 14 is a further expanded, partial cross-sectional view of the display hub of the occlusion catheter of FIG. 1A.
Figure 15:
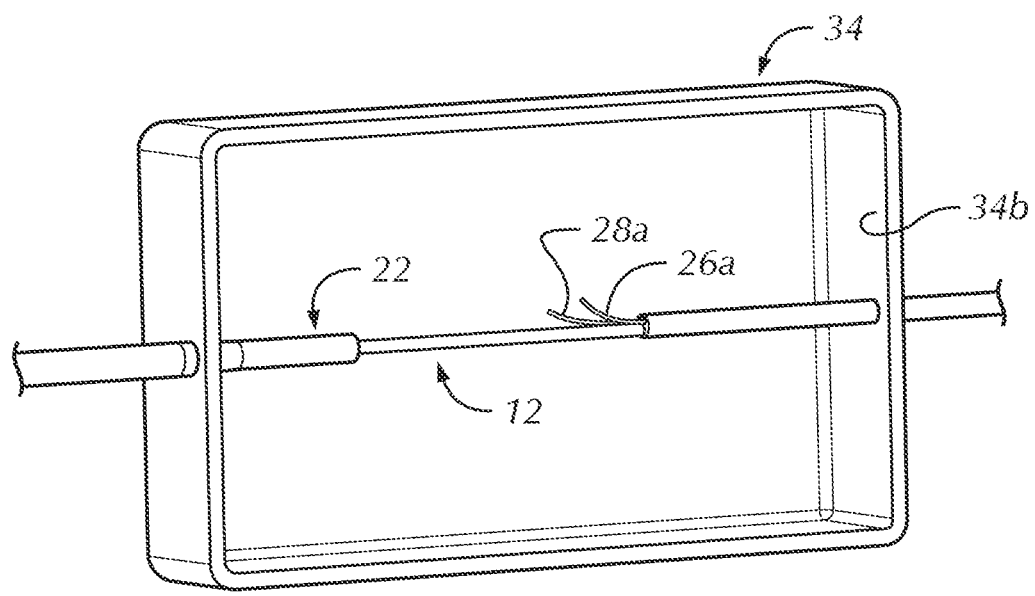
FIG. 15 is a partial perspective view of the display hub of the occlusion catheter of FIG. 1A, exposing the proximal catheter shaft extending therein.
Figure 16:
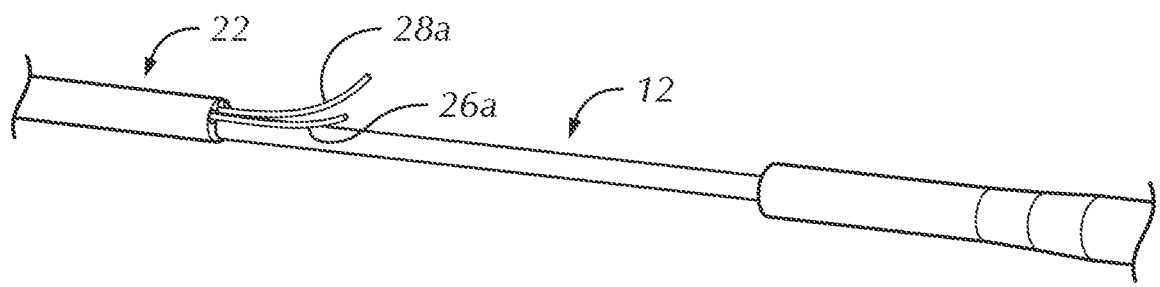
FIG. 16 is a partial perspective, isolated view of a portion of the proximal catheter shaft of the occlusion catheter of FIG. 1A, exposing sensor wires therein.

As shown, the hypotube 12 extends through the display hub 34 and to the inflation hub 14. In one configuration, as shown in FIG. 13, the outer proximal shaft 22 begins at a distal end of the display hub 34. Alternatively, as shown in FIG. 15, the outer proximal shaft 22 may extend into the display hub 34. The display hub 34 is stabilized to the outer proximal shaft 22 and the hypotube 12 via any of numerous fastening methods currently known, or that later become known, to those of ordinary skill in the art. FIGS. 15 and 16 illustrate exposure of the proximal and distal sensor signal wires 26a, 28a, within the display hub 34, for operative, e.g., electronic, connection with the main circuit board 34c, to enable display of the detected data.

A display hub enclosure 34b, such as, without limitation, a two-part clamshell enclosure, houses the display electronics. In one configuration, the display hub enclosure 34b may be water resistant and/or waterproof. For example, a gasket may be interposed between the two-part clamshell enclosure. Display electronics include, but are not limited to, the display hub enclosure 34b may include a main circuit board 34c, e.g., a printed circuit board, a power source 34d, e.g., a battery, a daughter board 34e, a display connector 34f, and the like. The display hub enclosure 34b may also include at least one depressible button 34f, permitting a user to select the desired display setting. The display hub enclosure 34b may also house electronics configured to transfer the display, e.g., via a wired or wireless connection, to a remote display. As should be understood, a wired connection may include, but is not limited to, an optical connection, e.g., a fiber optic cable, a USB connection or the like. Such a cable may be connected to the display hub 34 via, for example, a 3.5 mm port, a USB port or the like. Display electronics may be placed generally centrally within the display hub enclosure 34b to maintain balance of the display hub 34. Alternatively, the display electronics may be generally equilibrated within the enclosure 34b to maintain balance.

Figure 17:
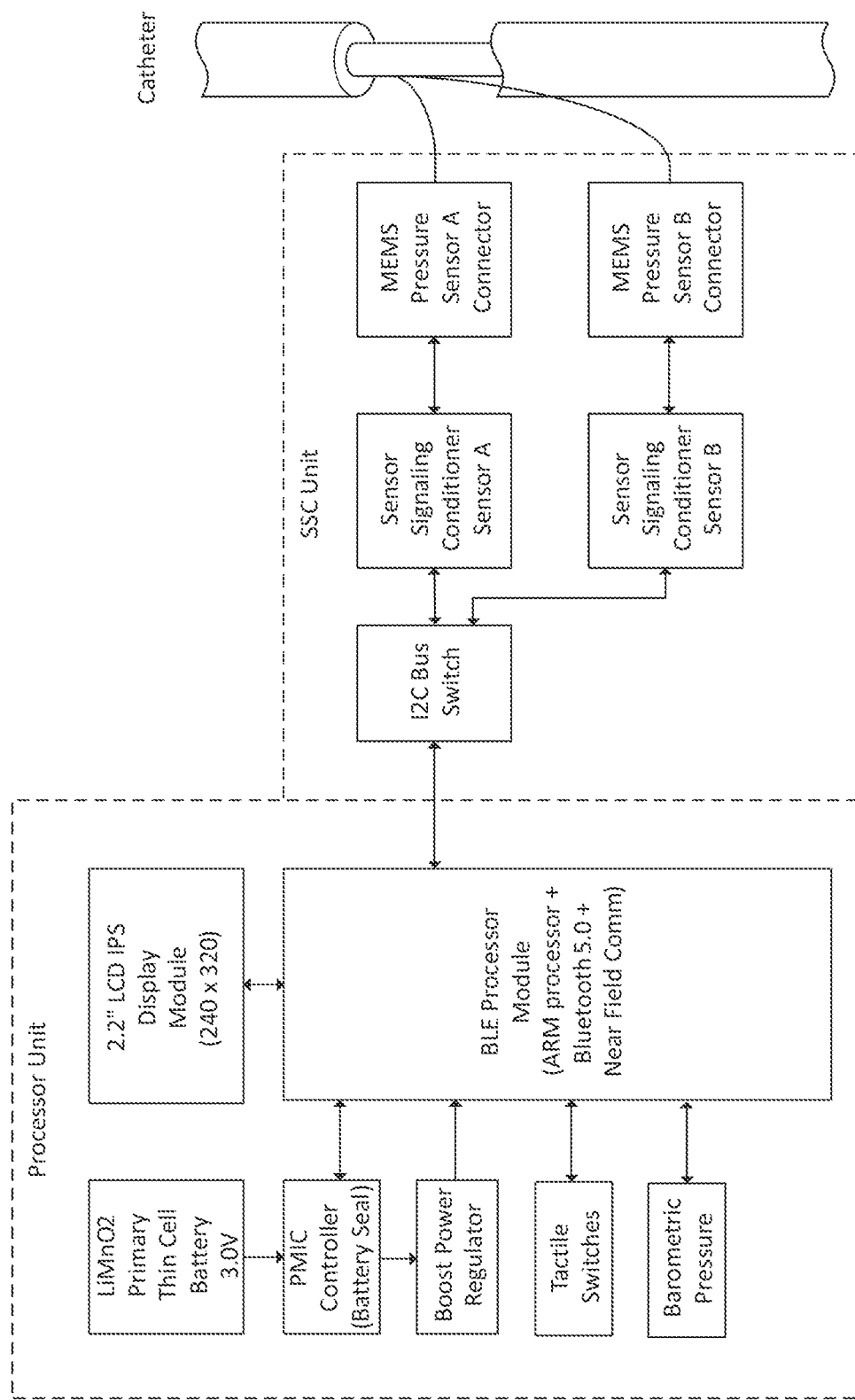
FIGS. 17-22 are schematic views of electronics of the display hub of the occlusion catheter of FIG. 1A.

In one configuration, as shown schematically in FIG. 17, the occlusion catheter 10 may include an integrated sterile, disposable, self-contained pressure transducer. Upon placement into a target vessel, e.g., the aorta, the invasive blood pressure (IBP), e.g., the central aortic pressure, is measured both distally and proximally to the occlusion balloon 16. As such, the display hub 34 may contain two printed wiring assemblies (PWA): one PWA, a sensor signaling conditioning (SSC) unit that interfaces to the transducer wires traversing the catheter and a second PWA, the processor unit that contains the processor, the display, battery, switches, barometric pressure and power management circuitry. The SSC unit measures the analog signal coming from each blood pressure transducer 26, 28, converts the analog signal into digital data and stores the data until read by the processor unit. Particularly where absolute pressure sensors 26, 28 are employed, the processor unit contains a barometric pressure transducer that allows the absolute pressure transducer data obtained by the SSC to be converted to the gauge-based blood pressure data, i.e., to measure and subtract off atmospheric pressure from the absolute pressure transducer data, for display on the screen or a vital signs monitor.

Figure 18:
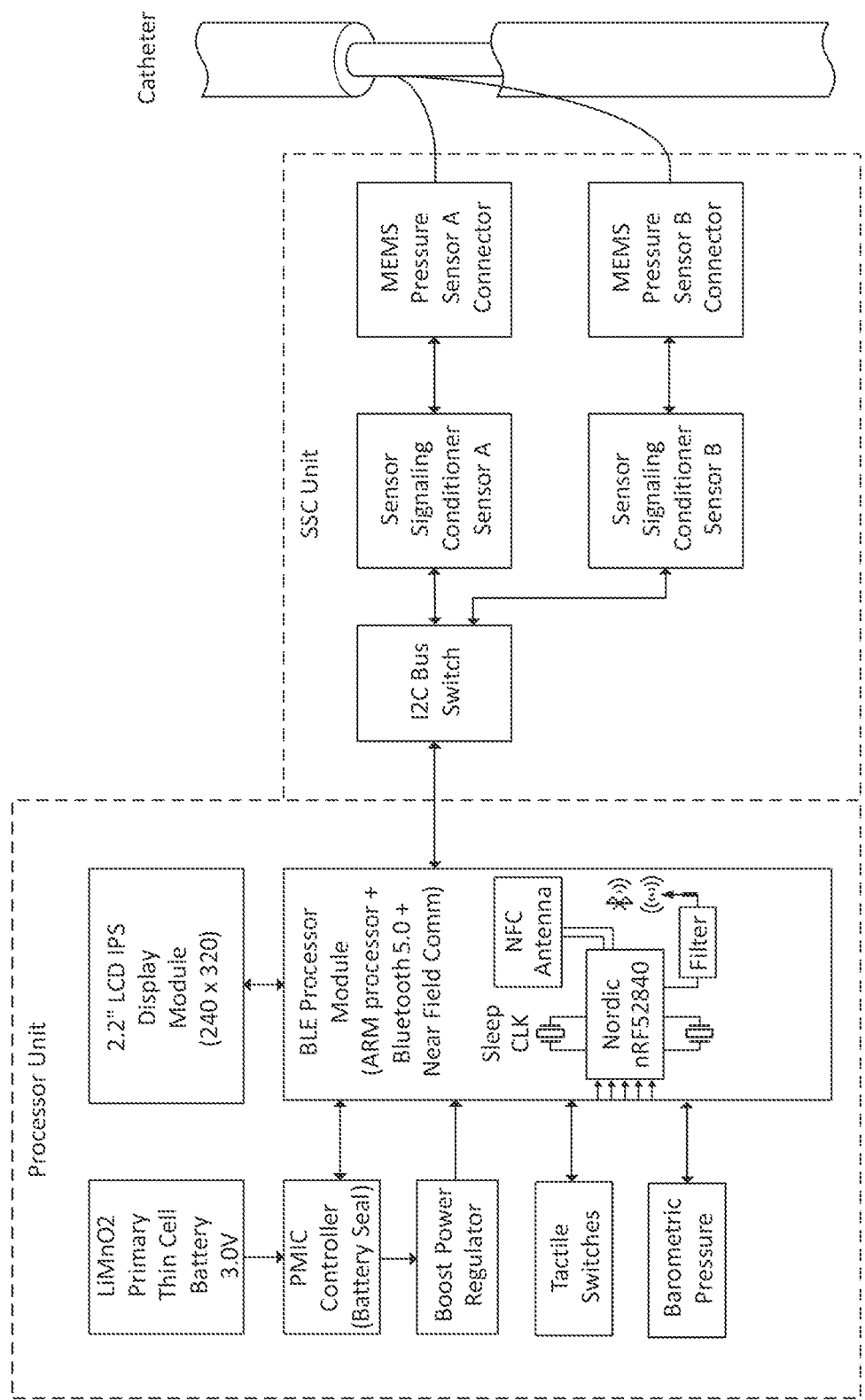

As shown schematically in FIG. 18, configurations of the display hub 34 may also include the ability to transmit the pressure data to another device such as a dangle connected to a vital signs monitor. The processor module is capable of transmitting data using Bluetooth Low Energy, IEEE 802.15.4 Thread, Zigbee wireless protocols and the like. The device processor module may contain an embedded crytocoprocessor to provide a secure connection and prevent denial of service attacks and other hacking measures. Such a configuration of the display hub 34 may also perform out-of-band (OOB) pairing. OOB pairing uses information that has been securely shared previously in place of a key for passkey entry for secure Bluetooth communications. The display hub 34 can communicate using near field communication (NFC) to share data needed for OOB pairing thus providing a convenient and secure method of establishing Bluetooth connections with other Bluetooth enabled devices. This can be done by simply tapping the display hub 34 against an NFC-enabled secondary device (e.g., BLE vital signs dongle). The short range of NFC communications aids both security and selectivity.

Figure 19:
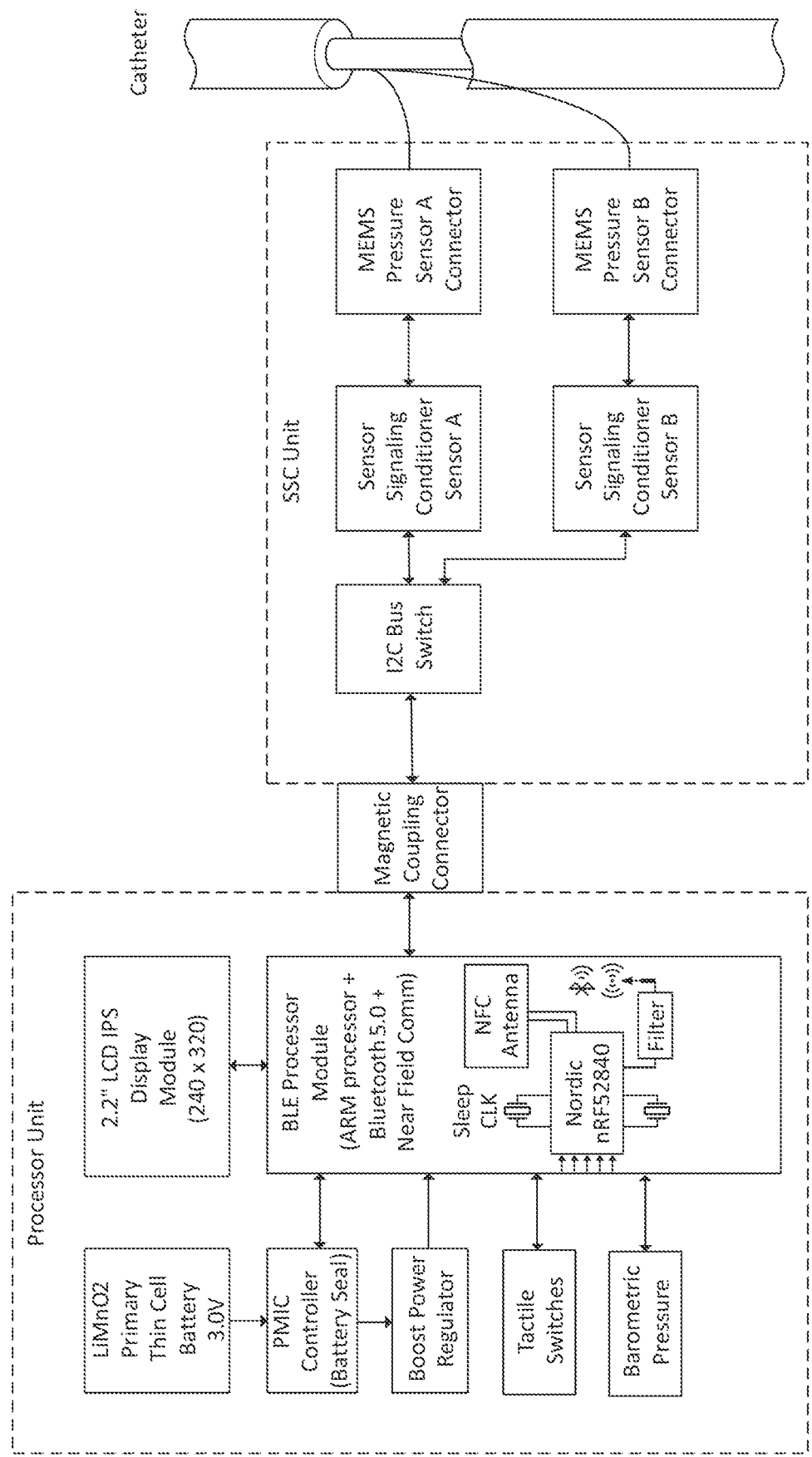

As shown schematically in FIG. 19, the display hub 34 may also include the ability to separate the processor unit from the SSC unit to allow the processor unit to be interchanged with other processor units having a variety of optional capabilities. The display hub 34 may have embedded in the SSC unit to provide the ability of matching the MEMS pressure transducers (e.g., sensors 26, 28) embedded in the catheter 10 to each of the two SSCs on the SSC unit. The Sensor Signaling Conditioner A and B each contain non-volatile memory to store the calibration data that provides the matching parameters between each sensor and SSC device. Accordingly, the processor unit can be installed onto the catheter and communicate to the SSCs via data bus protocols, such as an I2C bus, a serial peripheral interface (SPI), one-wire (OWI) or the like. This provides the user/practitioner the ability to remove the processor unit to exchange the battery in case the battery is drained. This also provides a processing unit with a variety of capabilities such as a processing unit without a screen that could replace one with a screen once the patient has reached a hospital trauma bay that has a processor unit that has been pre-paired with a vital sign dongle connected to the trauma bay's vital signs monitor. The method of coupling the processor to the SSC unit could be via magnetic pogo-pin connectors or mechanically secured via a clip or some other quick release fastener. The display hub 34 may also be configured to wirelessly transmit the sensor data to a separate display, e.g., a tablet or vital signs monitor. The display hub 34 may also be configured to wirelessly transfer the sensor data to a controller accessory. Additionally, or alternatively, a controller accessory may be integrated into the display hub 34.

Figure 20:
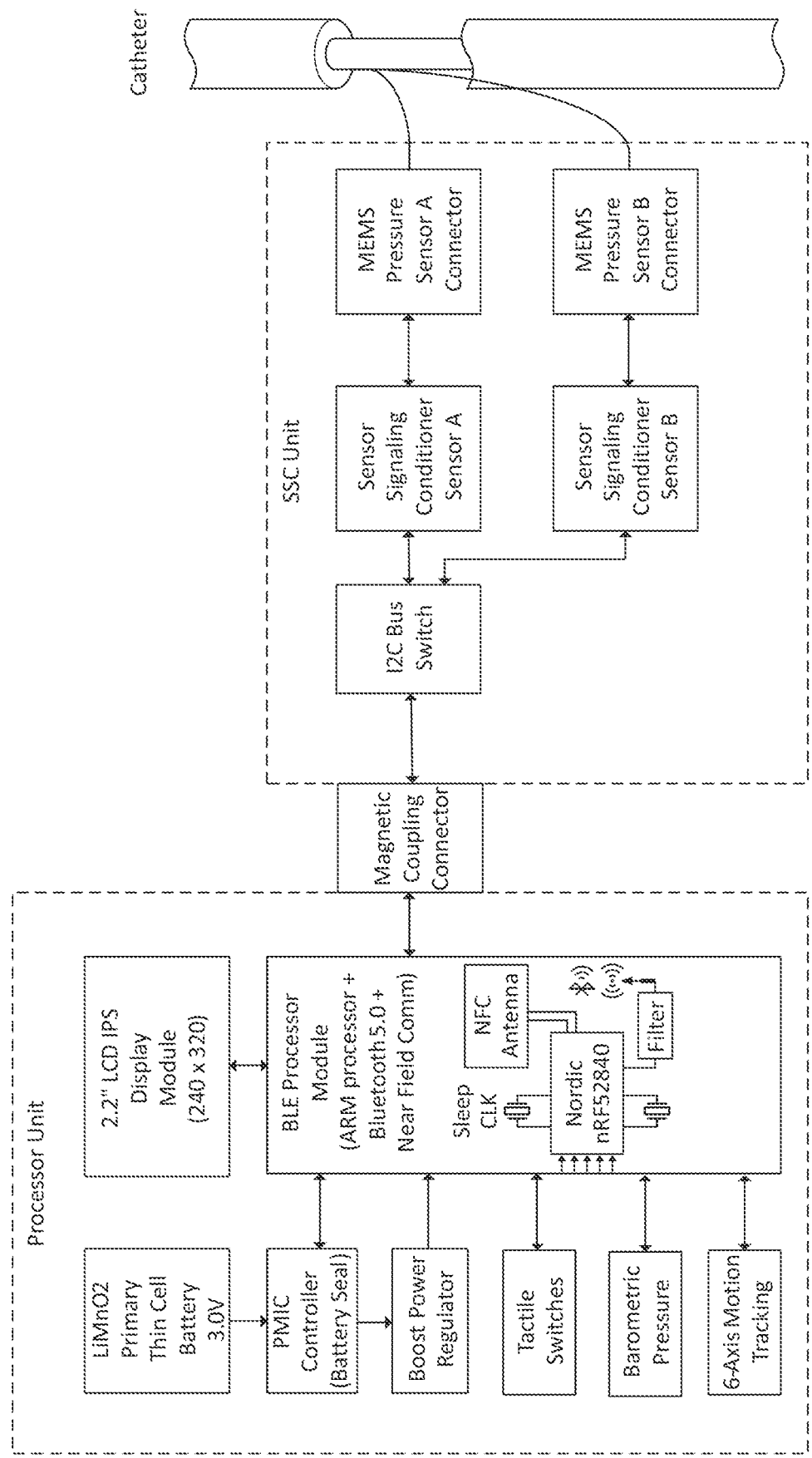

In one configuration, as shown schematically in FIG. 20, additional features may be included into the processor unit. For example, a 3-axis inertial measurement unit or a 6-axis inertial measurement unit motion tracking component on the processor PWA may be included, that provides enclosure orientation data to the processor unit. This allows the processor unit to display data in the correct orientation knowing which direction is up on the display or to switch between landscape and portrait modes based on viewing orientation. This feature can also be used to wake the device by slightly shaking the device awake if placed in a sleep mode to conserve battery life. Screen backlight is a battery draining component on the processor unit. By slightly shaking the device, the backlight may be returned from a lower power mode (dim) to fully awake mode (high brightness). Shaking the device can also place the device into a Bluetooth pairing mode using the NFC OOB operation previously described. The user may shake the device and immediately place it in close proximity to the vital signs dongle to pair the two devices via NFC OOB.

Figure 21:
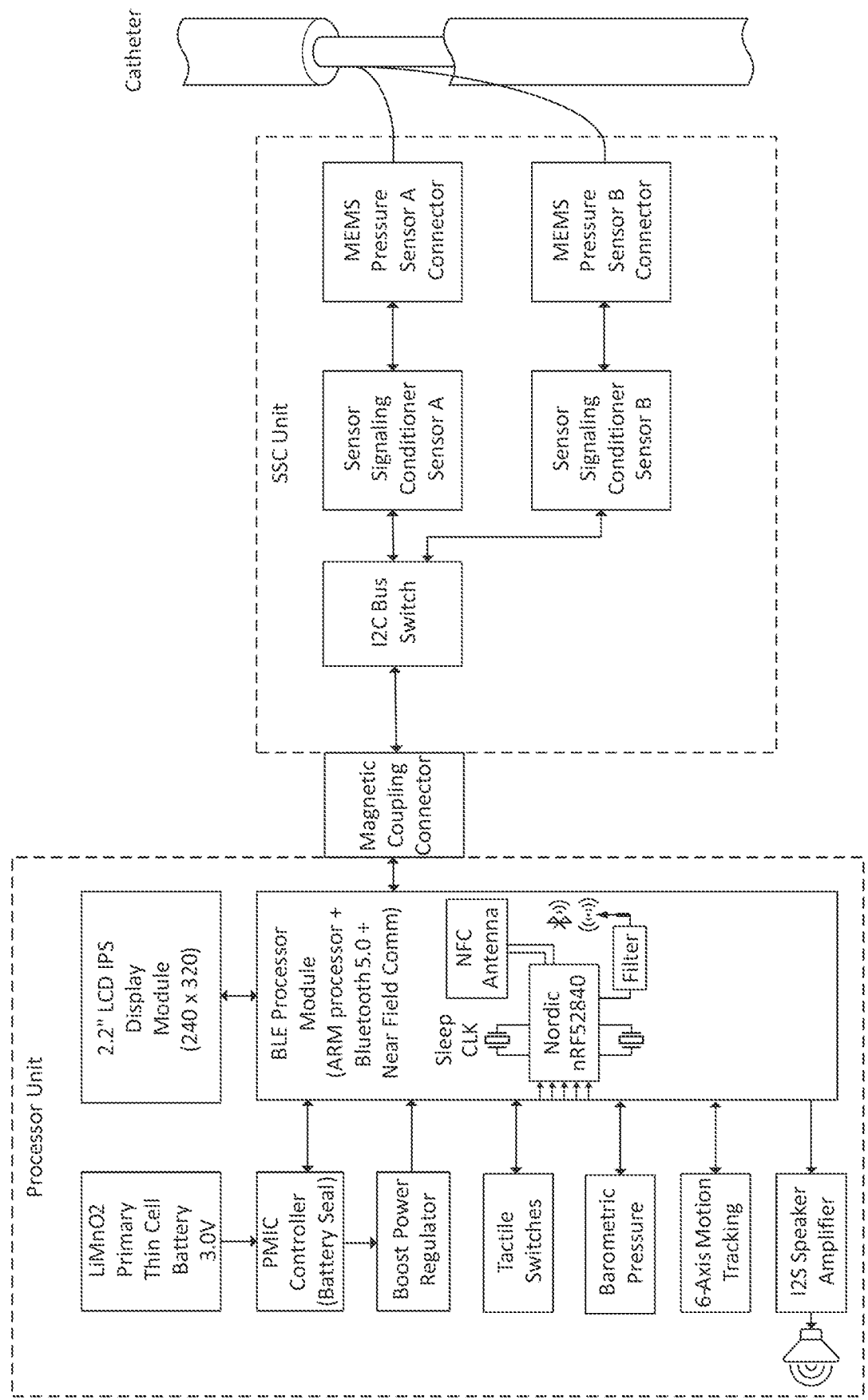
Figure 22:
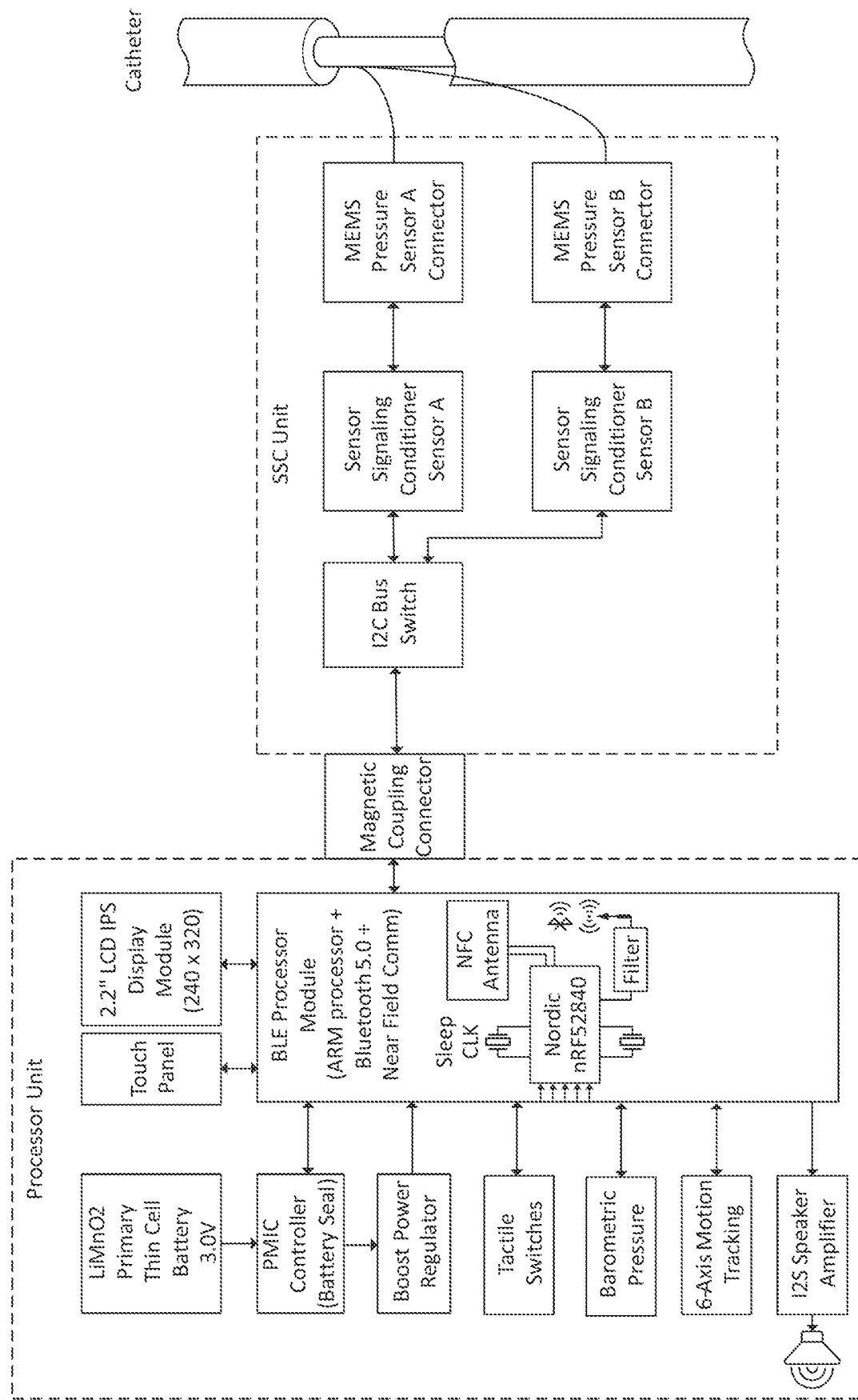

Another feature that may be included on the device is a speaker amplifier and speaker, as shown schematically in FIG. 21. This provides an ability for the device to provide audible notifications or alarms. It also provides for audible instructions on device usage in the same manner as an AED device provides audible voice prompts for user instruction. Yet another feature that may be included on the device is a touch panel interface for the screen, as shown schematically in FIG. 22. This provides another capability for the user to enter data into the device or navigate through a menu tree. The touch panel can be either of the resistive or capacitive type, providing either single or multi-touch operation.

FIGS. 26-29B illustrate a second embodiment of the occlusion catheter 110. The reference numerals of the present embodiment are distinguishable from those of the above-described embodiment by a factor of one-hundred (100), but otherwise indicate the same elements as indicated above, except as otherwise specified. The occlusion catheter 110 of the present embodiment is similar to that of the earlier embodiment. Therefore, the description of certain similarities between the embodiments may be omitted herein for the sake of brevity and convenience, and, therefore, is not limiting.

A primary difference between the first and second occlusion catheters 10 and 110 pertains to the inflation lumen. That is, the occlusion catheter 110 includes a hypotube 112 having an internal hypotube lumen 112a, a proximal catheter shaft 122 having a proximal shaft lumen 123, and a distal catheter shaft 118. The hypotube 112 extends axially through the proximal catheter shaft 122, through the occlusion balloon 116 and couples to the distal catheter shaft 118. The proximal shaft lumen 123 extends from, and is in fluid communication with, the inflation hub (not shown) and terminates within the occlusion balloon 116. Accordingly, inflation of the occlusion balloon 116 is provided via the free, annular space of the proximal shaft lumen 123 not occupied by the hypotube 112. Optionally, a guidewire (not shown) may be extendable through the hypotube lumen 112a and the distal catheter shaft 118 to an exit port 119 at the base of the atraumatic tip 120 in a manner well understood by those in the art.

Figure 26:
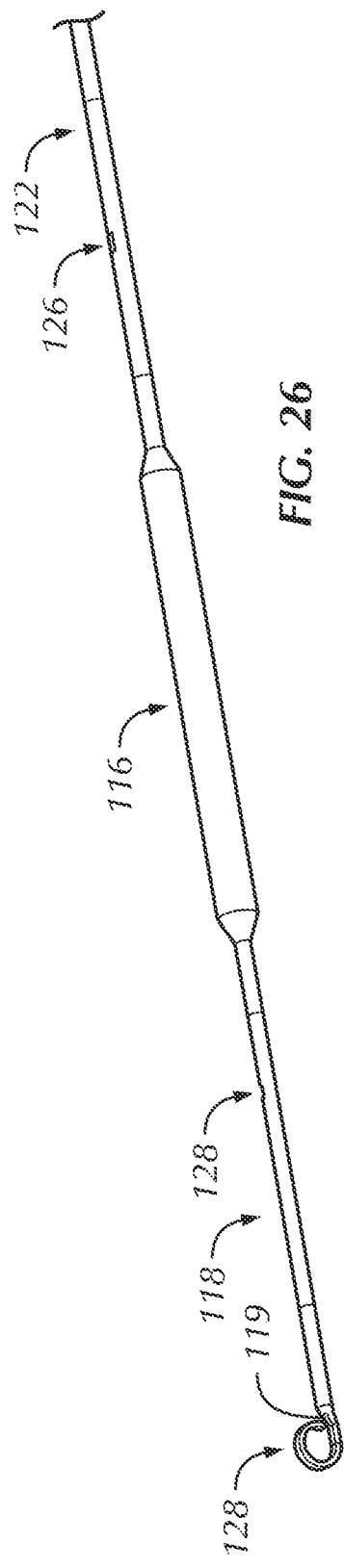
FIG. 26 is a partial, perspective view of an occlusion catheter according to a second embodiment of the present disclosure.
Figure 27:
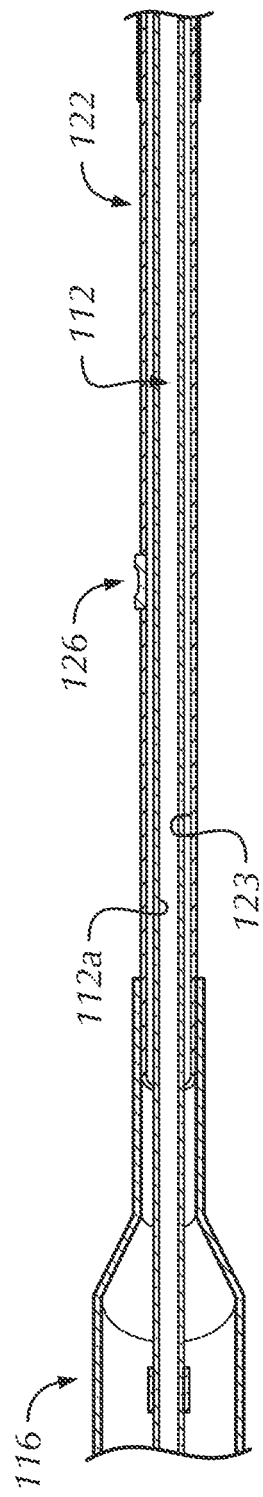
FIG. 27 is an expanded, partial cross-sectional view of a proximal section of the occlusion catheter of FIG. 26, taken along an axial axis of the catheter.

As shown best in FIG. 26, the occlusion catheter 10 includes a proximal and/or a distal sensor 126, 128. Similarly to the embodiment of the occlusion catheter 10, the proximal sensor 126 is positioned proximally of the occlusion balloon 116 and the distal sensor 128 is positioned distally of the occlusion balloon 116. The proximal and distal sensors 126, 128 may be pressure sensors, such as, for example, Micro Electro-Mechanical System ("MEMS") sensors, but the disclosure is not so limited (as described with respect to the embodiment of catheter 10).

Figure 28:
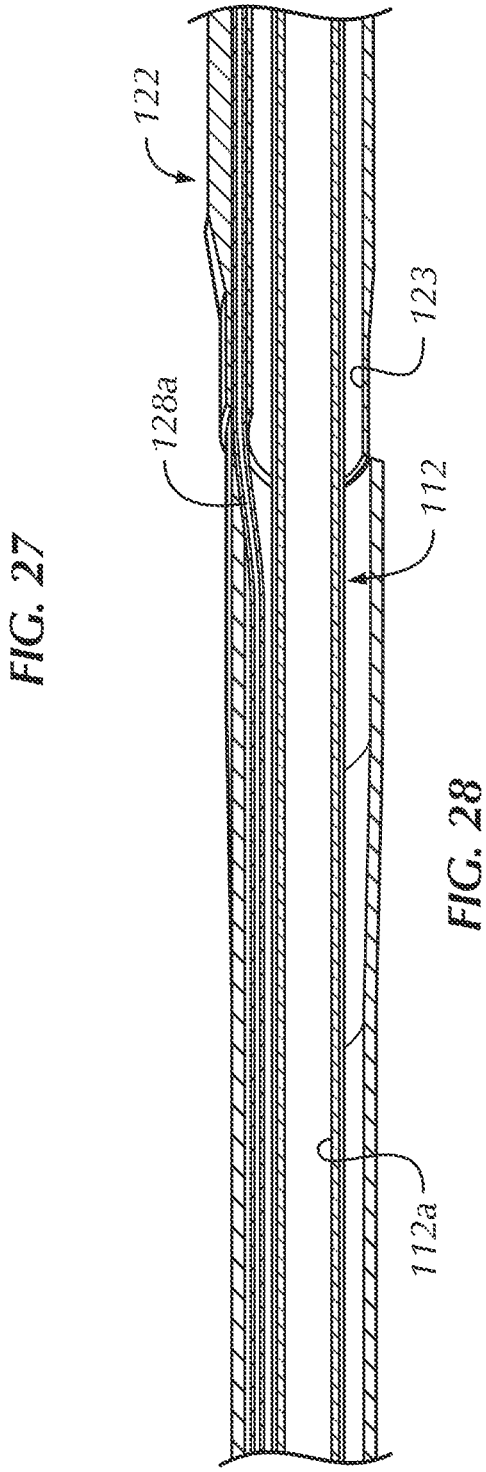
FIG. 28 is a further expanded and further partial cross-sectional view of a proximal section of the occlusion catheter of FIG. 26, taken along an axial axis of the catheter.
Figure 29A:
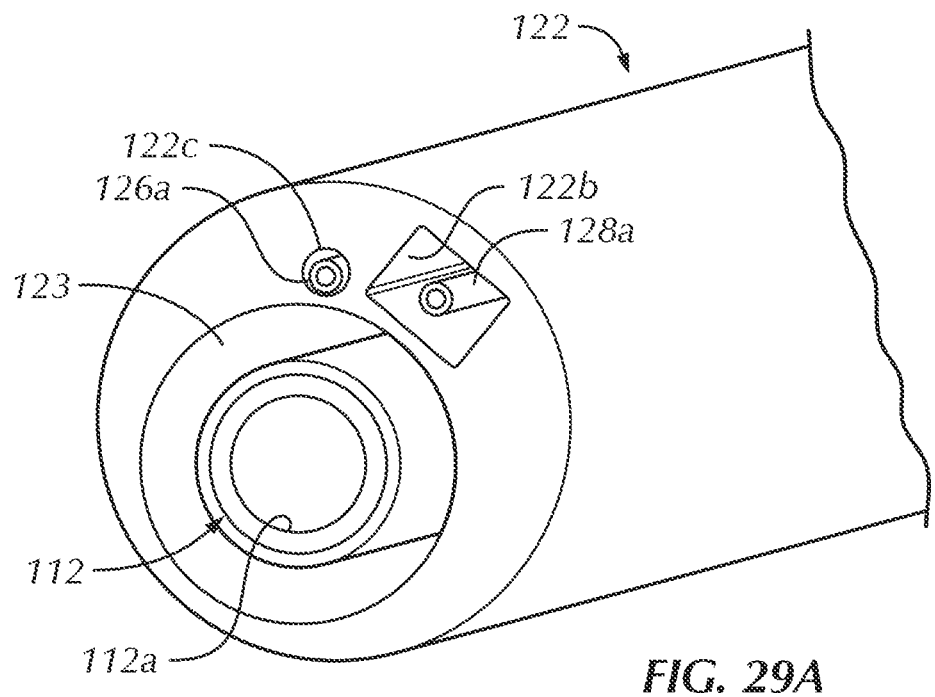
FIG. 29A is a perspective, cross-sectional view of the occlusion catheter of FIG. 26, taken through a proximal catheter shaft of the occlusion catheter.
Figure 29B:
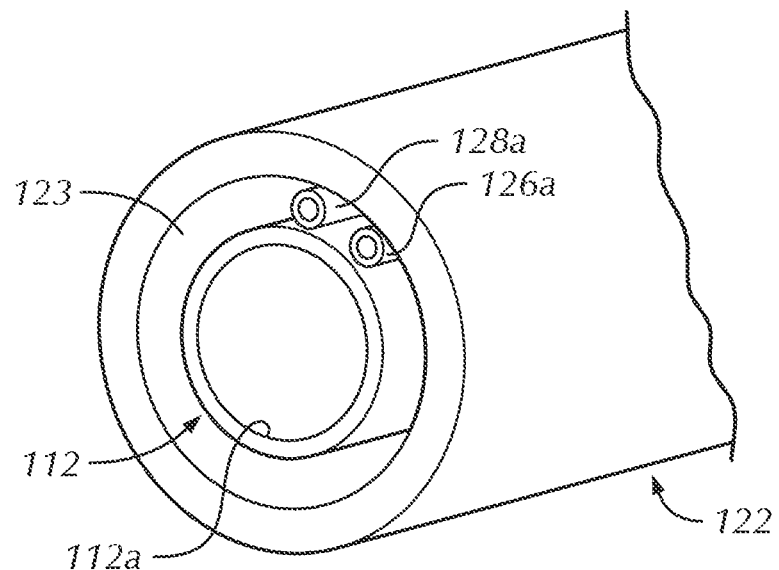
FIG. 29B is a perspective, cross-sectional view of the occlusion catheter of FIG. 26, taken through an alternatively configured proximal catheter shaft of the occlusion catheter.
Figure 30:
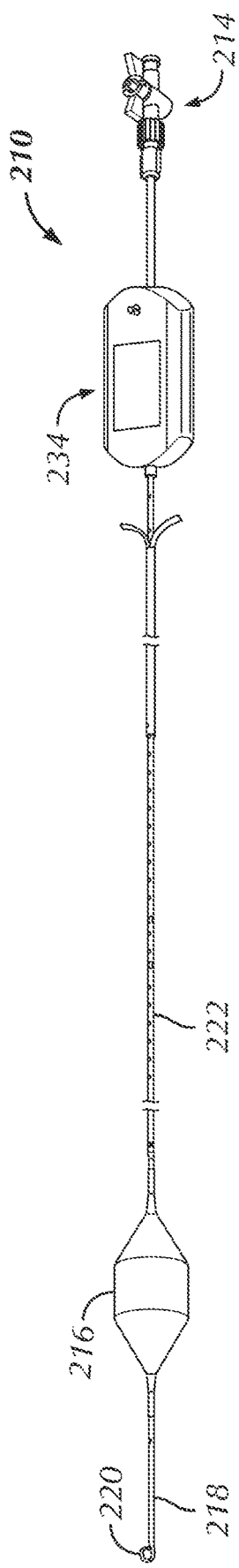
FIG. 30 is a perspective view of an occlusion catheter according to a third embodiment of the present disclosure.

The distal sensor wire 128a travels proximally from the distal sensor 128 and through the free, annular space of the proximal shaft lumen 123 through the occlusion balloon 116 (see FIG. 28). In one configuration, as shown in FIG. 29b, the distal sensor wire 128a may travel through the free, annular space of the proximal shaft lumen 123 all the way back to the hub (not shown). The proximal sensor wire 126a may also travel proximally from the proximal sensor 126 to the hub through the free, annular space of the proximal shaft lumen 123. In such configurations, one or all of the sensor wires, e.g., 126a, 128a, may be jacketed to the hypotube 112, e.g., via a shrink tube, at least for a partial extent of travel. Alternatively, as shown best in FIGS. 28, 29A, the distal sensor wire 128a may routes radially outwardly (proximally of the occlusion balloon 116) from the free, annular space of the proximal shaft lumen 123 and into a lumen 122b in the sidewall of the proximal catheter shaft 122 leading to the hub. The proximal sensor wire 126a may also travel proximally from the proximal sensor 126 to the hub through a lumen 122c in the sidewall of the proximal catheter shaft 122 leading to the hub. Alternatively, the proximal sensor wire 126a may be jacketed to an outside of the proximal catheter shaft 122. In one configuration, as shown in FIG. 29A, the lumens 122b, 122c may be differently dimensioned, but the disclosure is not so limited. As should be understood, the proximal catheter shaft 122 may include additional lumens in the sidewall thereof. Additionally, or alternatively, multiple sensor wires may travel through the same lumen in the sidewall thereof.

FIGS. 30-42 illustrate a third embodiment of the occlusion catheter 210. The reference numerals of the present embodiment are distinguishable from those of the above-described embodiments by a factor of two-hundred (200), but otherwise indicate the same elements as indicated above, except as otherwise specified. The occlusion catheter 210 of the present embodiment is similar to that of the earlier embodiments. Therefore, the description of certain similarities between the embodiments may be omitted herein for the sake of brevity and convenience, and, therefore, is not limiting.

Similarly to the occlusion catheters 10 and 110, the occlusion catheter 210 includes a first shaft/hypotube 212 forming the structural backbone/chassis of the catheter 210, an inflation hub 214 at a proximal end of the catheter 210, an expandable occlusion balloon 216, a generally hollow proximal outer shaft 222 proximal to the balloon 216 and a distal outer shaft 218 distal to the balloon 216 and distally terminating in an atraumatic tip or a P-tip 220.

The proximal outer shaft 222 may include multiple discrete internal lumens (e.g., multiple, discretely extruded lumens). The hypotube 212 extends axially through a first lumen of the proximal outer shaft 222, the proximal shaft lumen 223, through the occlusion balloon 216 and terminates within the distal catheter shaft 218. The proximal shaft lumen 223 is in fluid communication with the inflation hub 214 at a proximal end thereof (as will be described in further detail below) (see FIGS. 37, 38) and distally terminates within the occlusion balloon 216, e.g. within the proximal neck 216a of the balloon 216 or beyond. As shown best in FIGS. 32 and 33, at least the portion of the proximal shaft lumen 223 overlaps with a second, parallel lumen of the proximal outer shaft 222, the sensor lumen 222c, and defines a generally annular, e.g., crescent shaped, space 223a. Inflation of the occlusion balloon 116 is provided via the unoccupied portion of the space 223a of the proximal shaft lumen 223, i.e., the unoccupied space surrounding the hypotube 212. As shown, the proximal neck 216a of the occlusion balloon 216 is bonded (in a manner well understood by those of ordinary skill in the art) to the proximal outer shaft 22.

Figure 32:
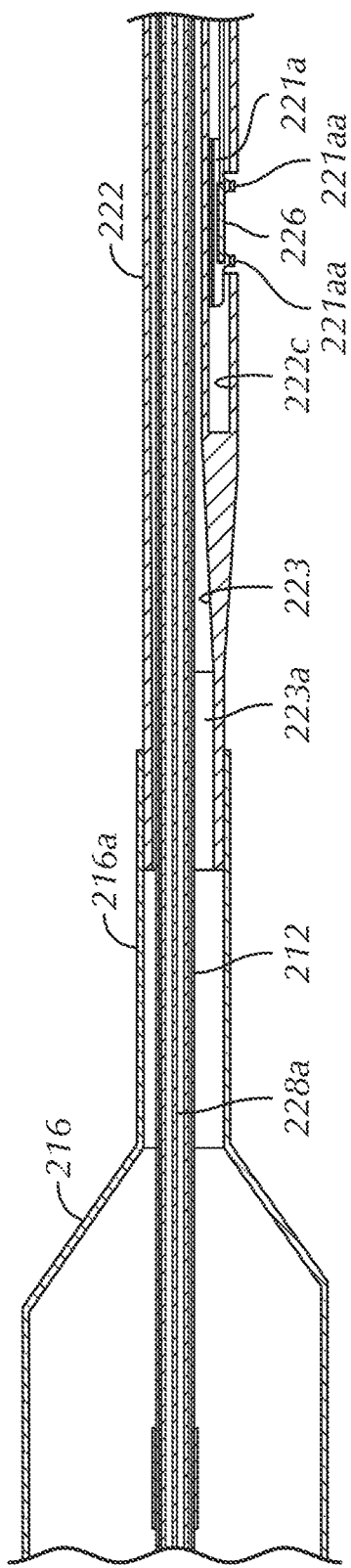
FIG. 32 is an expanded, partial cross-sectional view of a proximal section of the occlusion catheter of FIG. 30, taken along an axial axis of the catheter.
Figure 33:
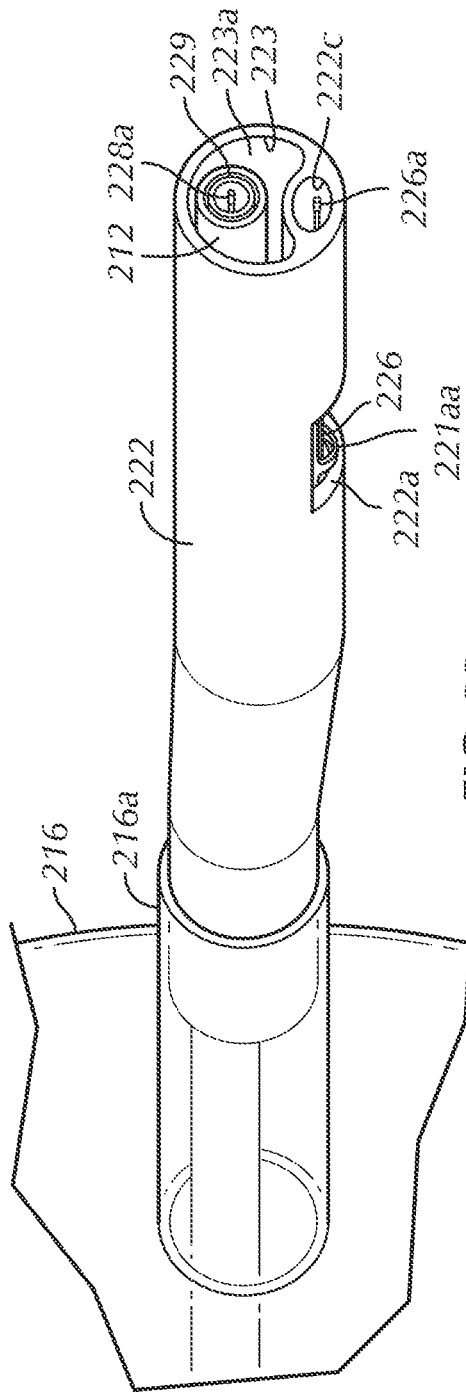
FIG. 33 is a perspective cutaway view of the proximal section of the occlusion catheter of FIG. 30.

A proximal sensor 226 may also be included in the occlusion catheter 210, proximal to the occlusion balloon 216. In such a configuration, and as also shown in FIGS. 32 and 33, the sensor lumen 222c is formed (proximally to the occlusion balloon 216) in the proximal outer shaft 222 and extends proximally at least along a portion of the axial length of the proximal outer shaft 222 to the display hub 234 (see FIGS. 37, 38). Alternatively, the sensor lumen 222c may be formed in the annular fill space 223a. A window 222a is formed in the sidewall of the proximal outer shaft 222 and extends into the sensor lumen 222c.

As shown best in FIGS. 32 and 33, the proximal sensor 226 is suspended in a first sensor case 221a sealingly mounted in the sensor lumen 222c and facing the window 222a. The first sensor case 221a is not cylindrical, however, but rather primarily half-cylindrical/half-pipe shaped. That is, the first sensor case 221a is generally U-shaped in cross-section (e.g., the sectional plane shown in FIG. 33) with two spaced apart connecting bands 221aa forming two discrete cylindrical portions of the first sensor case 221a. The two connecting bands 221aa, having a greater profile than the remainder of the first sensor case 221a, are configured to align with, and extend into, the window 222a. Advantageously, therefore, the sensor lumen 222c need only account for the lower profile half-pipe shape of the first sensor case 221a, resulting in a lower profile sensor lumen 222c. Advantages of a lower profile sensor lumen 222c include maintaining the overall low profile of the catheter 210 (7 Fr or less) as well as maximizing the size of the parallel inflation lumen 223a (in view of the maximum external diameter of the proximal outer shaft 222 (7 Fr or less). The proximal sensor signal wire 226a extends proximally from the proximal sensor 226 to the display hub 234 through the sensor lumen 222c.

Figure 34:
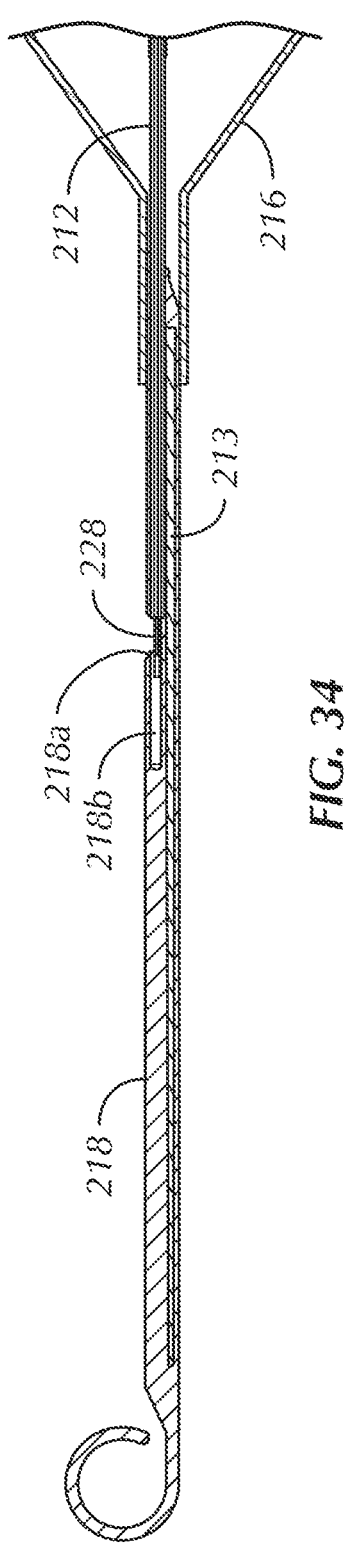
FIG. 34 is an expanded, partial cross-sectional view of a distal section of the occlusion catheter of FIG. 30, taken along an axial axis of the catheter.

Turning to the distal side of the occlusion balloon 216, the hypotube 212 extends through the occlusion balloon 216 and terminates within the distal outer shaft 218. The distal neck 216b of the occlusion balloon 216 is bonded (in a manner well understood by those of ordinary skill in the art) to at least one of the hypotube 212 and the distal outer shaft 218. As shown in FIG. 34, the distal outer shaft 218 includes a distal internal channel 218b extending along a portion of the distal outer shaft 218 from the proximal end thereof. The hypotube 212 extends into the distal internal channel 218b, and, therefore, is substantially coaxial therewith.

A distal sensor 228 may also be included in the occlusion catheter 210, distal to the occlusion balloon 216. In such a configuration, a second window 218a is formed in the sidewall of the proximal distal shaft 218 and extends into the distal internal channel 218b. The distal sensor 228 is positioned within internal distal channel 218b facing the second window 218a and the distal sensor signal wire 228a extends proximally from the distal sensor 228 along a portion of the internal distal channel 218b and through the hypotube 212 to the display hub 234.

Similarly to the proximal sensor 226, the distal sensor 228 is also suspended in a second sensor case 221b sealingly mounted in the internal distal channel 218b and facing the second window 218a. The second sensor case 221b may be of the same structure as the first sensor case 221a to provide the same benefits. That is, with respect to the distal sensor 228, the internal distal channel 218b need only account for the lower profile half-pipe shape of the second sensor case 221b and the size of the hypotube 212, enabling a lower profile internal distal channel 218b, and, in turn, furthering the overall low-profile objective of the catheter 210 (7 Fr or less).

Optionally, and as shown best in FIG. 33, the distal sensor signal wire 228a may be jacketed by an insulating polymeric tube 229 for protection of the wire, e.g., against an electrical short. As should be understood by those or ordinary skill in the art, the proximal sensor signal wire 226a may also be jacketed by a polymeric tube. In the configuration of the occlusion balloon catheter 210 of FIG. 31, employing both proximal and distal sensors 226, 228, the sensors 226 and 228 are positioned on generally diametrically opposed sides of the respective shafts 222, 218, but the disclosure is not so limited. That is, the catheter 210 may be formed to have one or both of the sensors 226, 228 anywhere along the circumference of the respective shaft 22, 218.

As previously described with respect to the catheter 10, in one configuration, where the proximal and distal sensors 226, 228 are pressure sensors, one or both of the proximal and distal sensors 226, 228 may take the form of an absolute sensor. Conversely, one or both of the proximal and distal sensors 226, 228 may take the form of a gauge sensor. In such form, the gauge sensor(s) needs to be vented to atmospheric pressure in order to provide the sensor itself with an atmospheric pressure reference. In one non-limiting, exemplary configuration, with respect to the distal sensor 228, the insulating polymeric tube 229, which proximally extends from the distal pressure sensor 228 and through which distal sensor signal wire 228a travels, may be routed to operate as a vent tube in communication with the distal pressure sensor 228 (as will be described in further detail below). In another non-limiting, exemplary configuration, with respect to the proximal sensor 226, the sensor lumen 222c, which proximally extends from the proximal pressure sensor 226 and through which proximal sensor signal wire 226a travels, may be routed to operate as a vent tube in communication with the proximal pressure sensor 226 (as will be described in further detail below).

Figure 35:
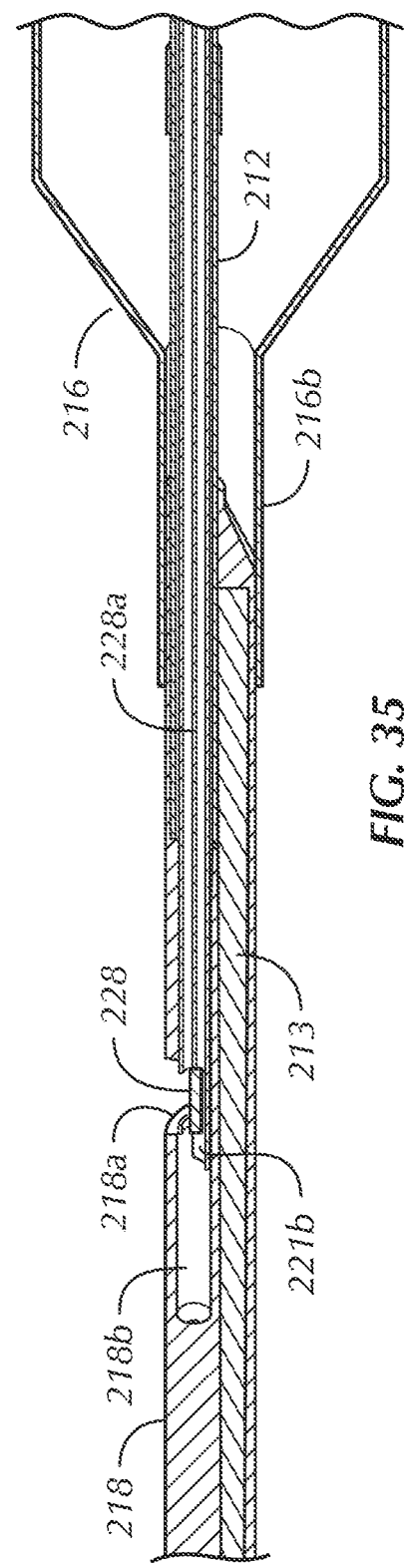
FIG. 35 is a further expanded, partial view of FIG. 34.

In one configuration, as shown best in FIGS. 34 and 35, a solid distal wire 213 is embedded in the distal outer shaft 218, but is positioned adjacent, and extends generally parallel, to the hypotube 212 and the internal distal channel 218b. That is, a proximal portion of the distal wire 213 overlaps with a distal portion of the hypotube 212 and is positioned adjacent thereto. Optionally, at least a section of the proximal portion of the distal wire 213 overlapping the distal portion of the hypotube 212 may be jacketed to the hypotube 212 by a polymeric sleeve or by the distal outer shaft 218 itself. The distal wire 213 may alternatively be welded or otherwise bonded to the hypotube 212, i.e., affixed without relying on a jacket. Similarly to the distal wire 13, the distal wire 213 may extend toward a distal end of the catheter 210 and taper from a proximal end thereof to a distal end thereof, thereby progressively reducing stiffness of the catheter 210 from the proximal end of the distal outer shaft 218 to the distal end thereof, e.g., due to a natural progressive strain relief proportional to the decreasing thickness the wire 213, thereby assisting with maneuverability of the catheter 210. As shown in FIGS. 34 and 35, the distal sensor 228 is positioned proximate the proximal end of the solid distal wire 213, which is of greater thickness than the distal end thereof. Advantageously, the proximal end of the distal wire 213 provides sufficient local flexural/bending strength underlying the distal sensor 228 to minimize sensor deflection that may otherwise impact sensor measurements. Alternatively, the distal wire 213 may be formed having a substantially constant cross-sectional dimension and exhibit the naturally increasing bending characteristics of a cantilevered arm along the length thereof. As previously described with respect to the solid distal wire 13, the solid distal wire 213 may also be constructed of the same material as the hypotube 12, 212 or may be constructed of another one of the suitable hypotube materials previously identified. Such materials, such as, for example, without limitation, nitinol, have super-elastic properties providing advantageous kink resistance. In view of the termination of the hypotube 212 in the proximal end of the distal outer shaft 218, the partial overlap of the solid distal wire 213 with the terminal end of the hypotube 212 in combination with the taper of the solid distal wire 213 provides kink-resistance to the distal end of the catheter 210 beyond the distal, terminal end of the hypotube 212.

Figure 36:
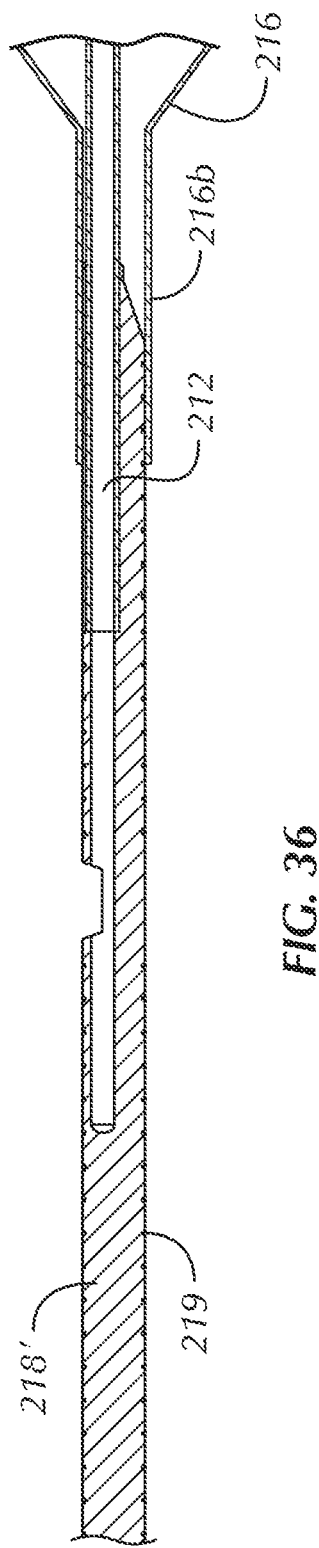
FIG. 36 is an expanded, partial cross-sectional view of an alternative configuration of the distal section of the occlusion catheter of FIG. 30, taken along an axial axis of the catheter.
Figure 37:
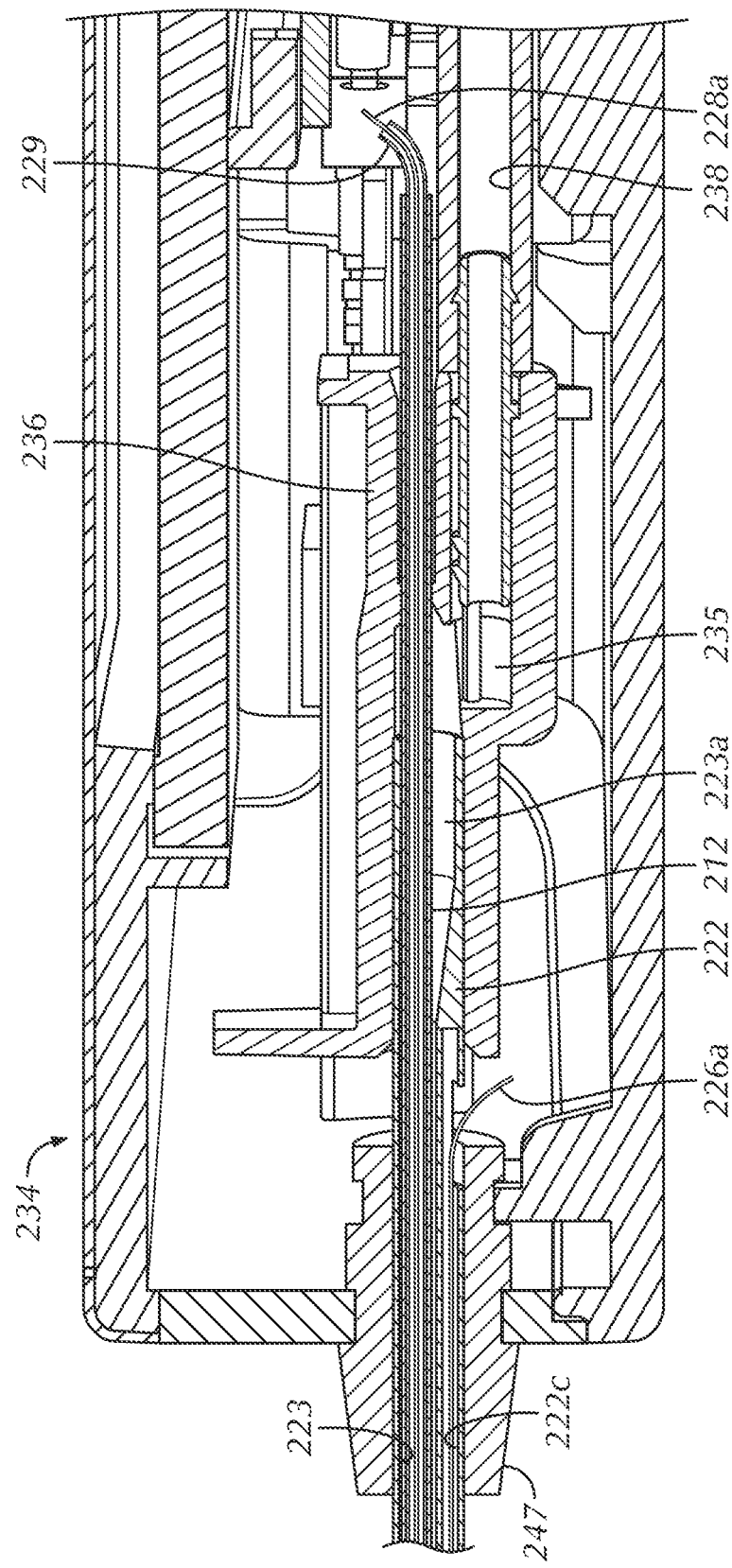
FIG. 37 is an elevational, partial, cross-sectional view of a display hub of the occlusion catheter of FIG. 30.
Figure 38:
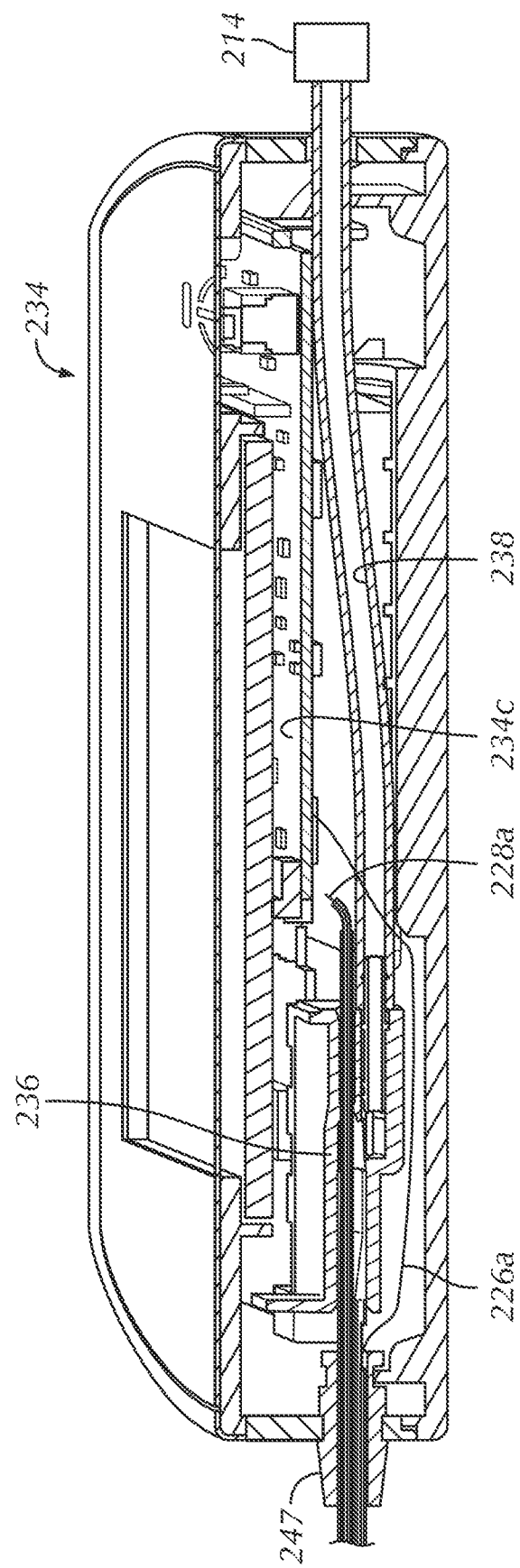
FIG. 38 is a perspective, cross-sectional view of the display hub of the occlusion catheter of FIG. 30.

In an additional or alternative configuration, as shown in FIG. 36, at least a portion (or the entirety, up to and including the atraumatic tip) of the distal outer shaft 218' may take the form of a braided shaft, e.g., having braiding 219 constructed of metal, such as stainless steel or nitinol, or synthetic fiber, such as Kevlar® or carbon fiber, a combination thereof, or the like, embedded in the sidewall of the shaft 218'. Similarly to the distal wire 213, the braiding 219 also overlaps a distal end of the hypotube 212 and continues along the distal outer shaft 218', thereby providing structural support along the length of the distal outer shaft 218'. Advantageously, and as previously described, such configurations employing one or both of the embedded, tapered distal wire 213 and the braided distal outer shaft 218' provide kink-resistance to the distal end of the catheter 210 beyond the distal, terminal end of the hypotube 212.

FIGS. 37-42 illustrate a configuration of the display hub 234. The display hub 234 may be configured as a water-resistant or waterproof hub, wherein gaskets are employed to prevent liquid ingress into the enclosure 234b, e.g., a gasket between the upper and lower halves of the clamshell enclosure, a gasket 247 surrounding the inflation shaft 238 at the point of entry into the enclosure 234b, a gasket 247 surrounding the proximal outer shaft 222 at the point of entry into the enclosure 234b, and surrounding other ports. As shown, the display hub 234 houses an internal hub frame 236, which operates as a load-bearing chassis of the display hub 234, including securing the enclosure 234b to the catheter 210. For example, the internal hub frame 236 structurally supports components of the display hub 234, such as, without limitation, the circuit board(s), power supply components, and other electronics. The internal hub frame 236 also secures the proximal outer shaft 222, the hypotube 212 and an inflation shaft 238 extending from the inflation hub 214. The internal hub frame 236 also fluidly connects the inflation shaft 238 with a proximal end of the generally annular fill space 223a of the proximal shaft lumen 223. Stated differently, the proximal shafts of the catheter 210 (e.g., proximal outer shaft 222 and the hypotube 212) are secured to the display hub 234 via the internal hub frame 236.

As shown, an outlet of the inflation shaft 238 is sealingly connected to the internal hub frame 236, e.g., via a barbed connection. An inlet of the proximal shaft lumen 223 is also connected to the inflation hub frame 236, e.g., via bonding or the like. The internal hub frame 236 fluidly connects the inflation shaft 238 with the proximal shaft lumen 223, e.g., via a dedicated channel 235 therein. As shown, the channel 235 may be non-linear. The inflation shaft 238 extends from the inflation hub 214 (shown schematically in FIG. 38), and, thereby, completes the fluid connection between the inflation hub 214 and the occlusion balloon 216. As shown, the proximal sensor signal wire 226a and the distal sensor signal wire 228a each connect with the main circuit board 234c. In the illustrated configuration, the distal sensor signal wire 228a extends through the internal hub frame 236, but the disclosure is not so limited. As should be understood, neither or both of the signal wires 226a, 228a may extend through the internal hub frame 236 to connect with the main circuit board 234c.

Figure 40:
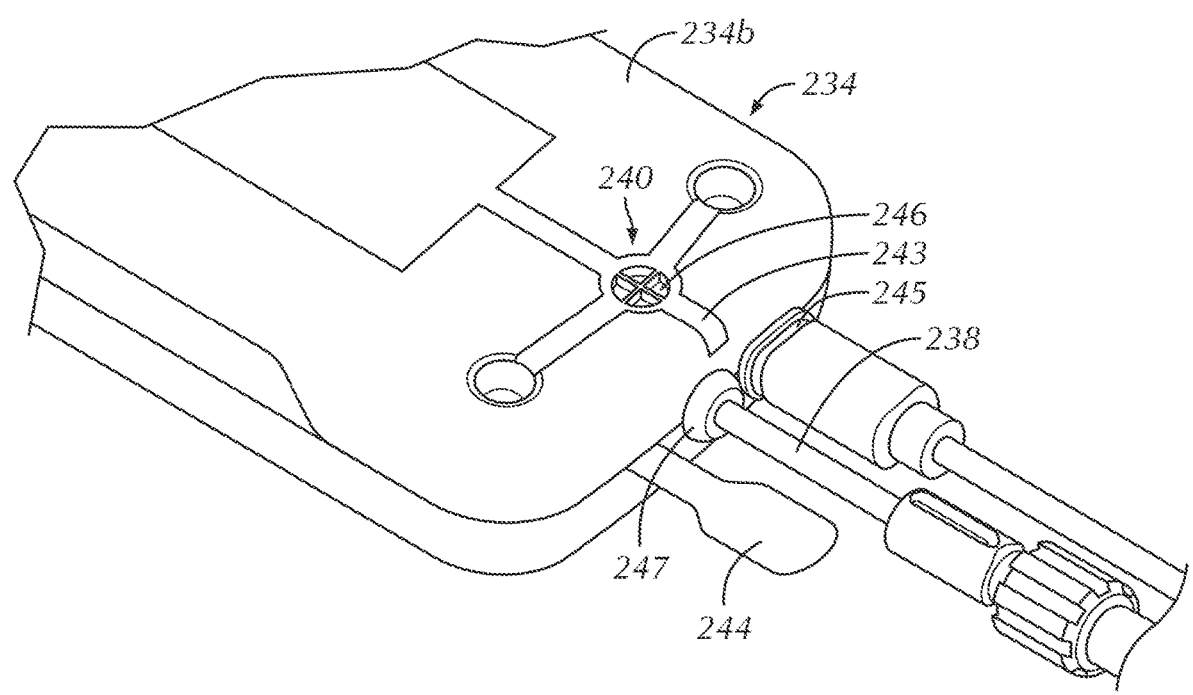
FIG. 40 is a partial, bottom perspective view of the display hub of the occlusion catheter of FIG. 30.
Figure 41:
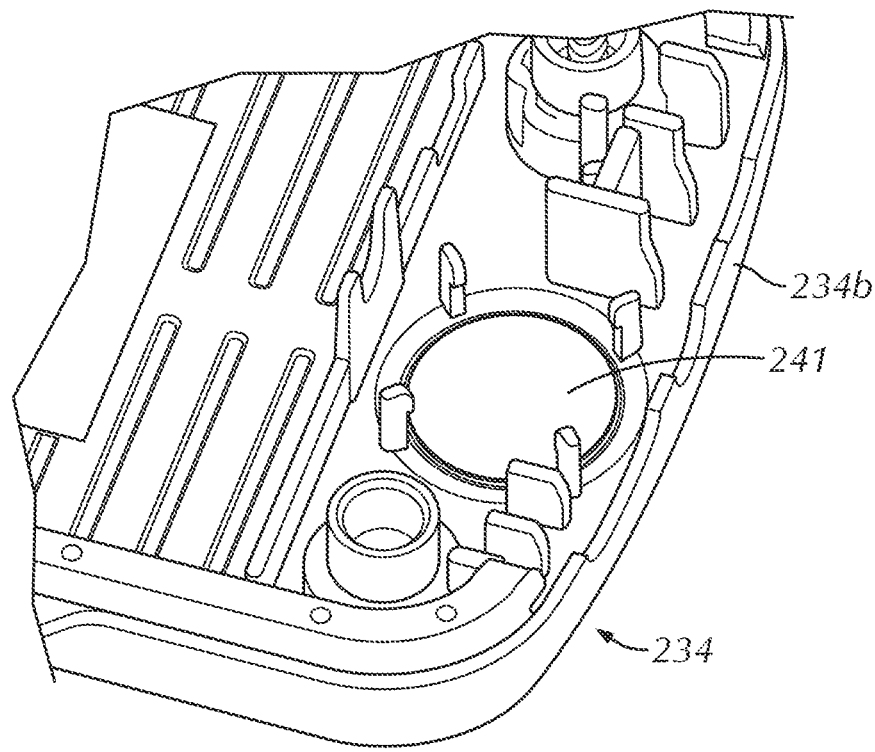
FIG. 41 is a partial, perspective internal view of one side of the clamshell enclosure of the display hub of the occlusion catheter of FIG. 30.
Figure 42:
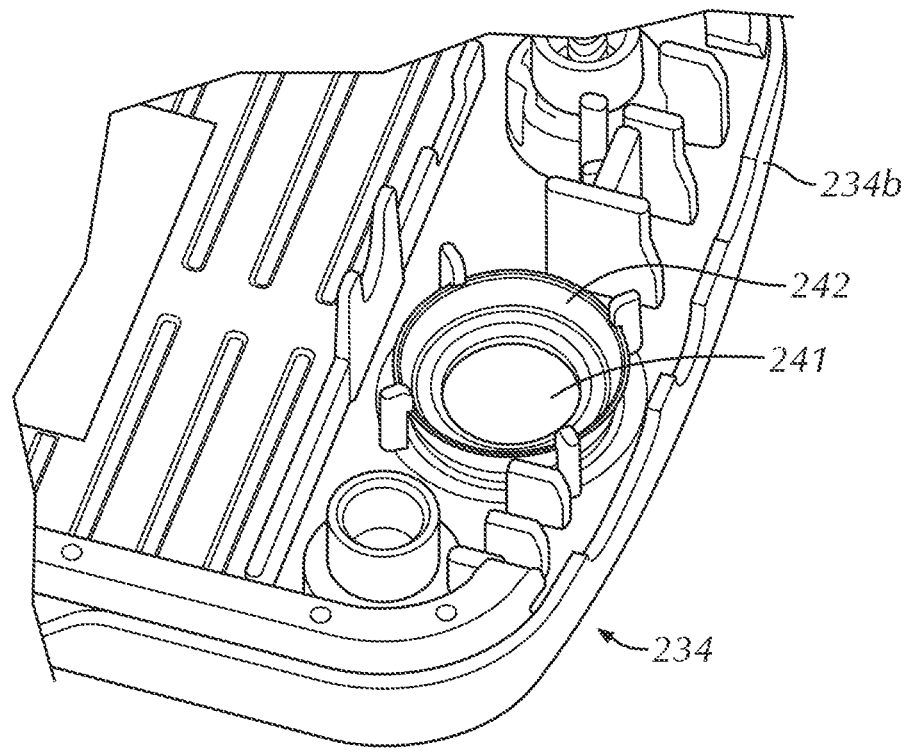
FIG. 42 is another partial, perspective internal view of one side of the clamshell enclosure of the display hub of the occlusion catheter of FIG. 30.

As shown in FIGS. 40-42, the display hub 234 may include a vent port 240. The vent port 240 includes at least one thru-hole 246 extending through the enclosure 234b of the display hub 234. Internally, as shown in FIGS. 41 and 42, the thru-hole(s) 246 is sealingly covered with a layer 241 of liquid impermeable (waterproof), breathable material, such as, without limitation, PTFE, ePTFE, Porex™, Gore-tex™ or the like, i.e., permitting the passage of gas, such as air, therethrough, and repelling the passage of liquid therethrough. The layer 241 is positioned in sealed engagement with the internal surface of the enclosure 234b of the hub 234 at a position underlying the thru-hole(s) 246. In one configuration, the layer 241 may be adhered to the internal surface of the enclosure 234b of the hub 234. Additionally, or alternatively, a retainer washer/clip 242 may be positioned upon the layer 241 via a snap-fit connection or the like to further maintain the seal between the layer 241 and the enclosure 234b.

Where an individual barometric pressure transducer is employed in the display hub 234, as previously described, the vent port 240 is fluidly connected to the pressure transducer to enable atmospheric pressure measurement. Where a gauge sensor is employed, as previously described, a lumen may be fluidly connected to the vent port 240. As one non-limiting example, one or both of the tube 229 and the sensor lumen 222c may be fluidly communicated with the vent port 240. As also should be understood, where a combination of absolute and gauge sensors are employed, both the barometric pressure transducer in the hub 234 and additional lumens may be fluidly communicated with the vent port 240.

Optionally, and as shown best in FIG. 40, the vent port 240 may be recessed from the outermost surface of the enclosure 234b, and at least one grooved channel 243 formed along the exterior of the enclosure 234b extends from the thru-hole(s) 246 to a periphery of the enclosure 234b. Advantageously, therefore, if the enclosure 234b is placed such that the vent port 240 faces on an underlying surface, or is otherwise inadvertently covered, the thru-hole(s) 246 may remain in fluid communication with the atmosphere via the grooved channel(s) 243.

Figure 39:
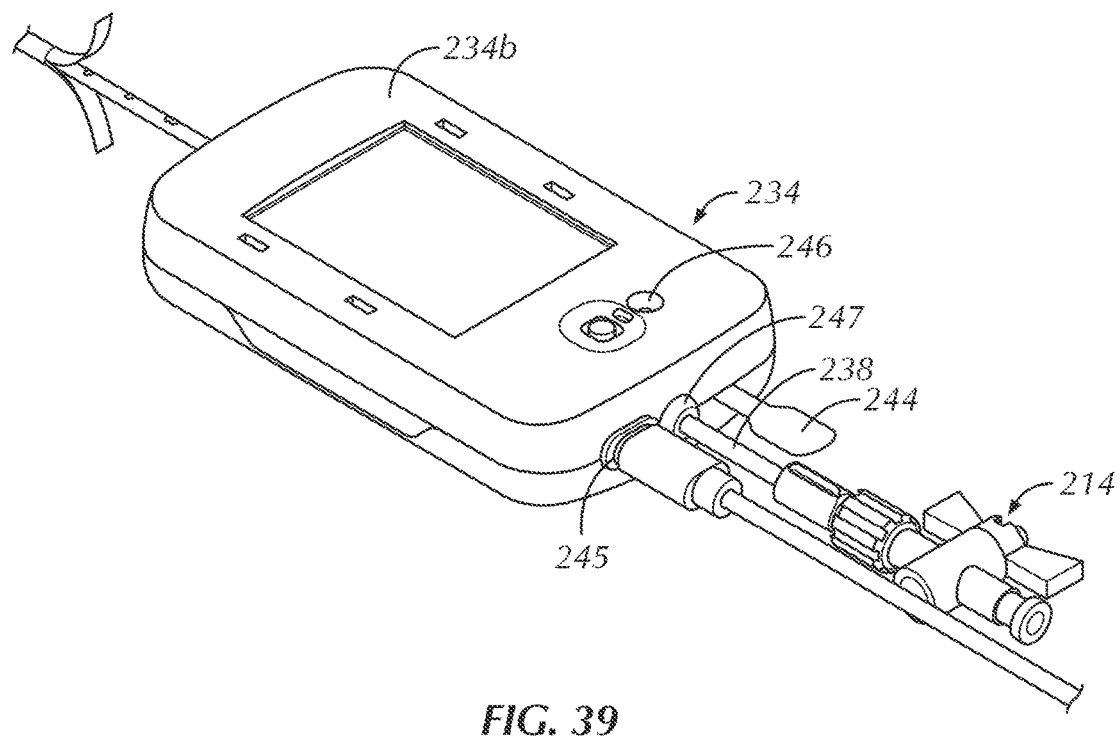
FIG. 39 is a top perspective view of the display hub of the occlusion catheter of FIG. 30.

As shown in FIGS. 39 and 40, the display hub 234 may also include a removable pull tab 244 interposed between opposing battery contacts or between contact points of a power circuit. As shown, the pull tab 244 extends from inside the enclosure 234b to an exterior thereof, e.g., between the upper and lower halves of the enclosure 234b. The pull tab 244 ensures disconnection of the battery (see, e.g. FIGS. 13. 14: 34d) within the display hub 234, particularly during sterilization thereof. Sterilization, e.g., via ethylene oxide sterilization, requires disconnection of the battery, which may otherwise pose a fire/explosion risk. Thereafter, the pull tab 244 may be removed to connect the power circuit of the display hub 234. For water-resistance/water-proofing of the enclosure 234b, the gasket between the upper and lower halves of the enclosure 234b is slit where the pull tab 244 exits to seal around the pull tab 244 when present, allow the passage of the pull tab 244 therethrough, and subsequently close to prevent liquid ingress after removal of the pull tab 244.

As shown in FIGS. 39 and 40, the display hub 234 also includes a data transmission port 245 configured for selective wired connection to a remote device (as previously described), e.g., a display, a controller, a combination thereof, or the like. In one configuration, the data transmission port 245 may be a USB port, but the disclosure is not so limited. In one additional or alternative configuration, the data transmission port 245 may be a water resistant or waterproof port, including being bound by a gasket to seal the data transmission port 245. When not in use, a plug (not shown) may be attached to the data transmission port 245. An ambient light sensor 246 may also be incorporated into the display hub 234.

It will be appreciated by those skilled in the art that changes could be made to the embodiment(s) described above without departing from the broad inventive concept thereof. For example, the proximal outer shaft 22, 122, 222 may be removed to further reduce the outer diameter of the occlusion catheter to, for example, six French (6 Fr), five French (5 Fr) or four French (4 Fr). It is understood, therefore, that this disclosure is not limited to the particular embodiments disclosed, but it is intended to cover modifications within the spirit and scope of the present invention, as set forth in the appended claims.

We claim:

1. A vascular occlusion catheter for at least partial occlusion of a target vessel having an internal vessel wall, the vascular occlusion catheter comprising:
   a proximal outer section;
   a distal outer section;
   a tip at a distal end of the catheter; and
   an occlusion balloon connected to the proximal outer section and the distal outer section;
   the proximal outer section having a first internal lumen and a second internal lumen, the first internal lumen being in fluid communication with the occlusion balloon;
   the distal outer section having a distal internal lumen;
   a hypotube having an internal hypotube lumen, the hypotube extending through the first internal lumen, through the occlusion balloon and into communication with the distal internal lumen, the hypotube operating as the primary load-bearing chassis of the vascular occlusion catheter;
   a solid distal wire embedded in the distal outer section and extending toward the tip, the solid distal wire having a central axis that is radially offset from a central axis of the hypotube;
   a first window formed in the proximal outer section;
   a proximal sensor being positioned within the second internal lumen facing the first window;
   a second window formed in the distal outer section;
   a distal sensor being positioned within the distal internal lumen facing the second window; and
   a display hub positioned along the proximal outer section, wherein the second internal lumen and the hypotube extend into the display hub, the display hub being electrically connected with the proximal sensor via the second internal lumen, and the display hub being electrically connected with the distal sensor via the internal hypotube lumen and the distal internal lumen.

2. The vascular occlusion catheter of claim 1, wherein the proximal sensor is a pressure sensor configured to measure central aortic pressure downstream of the occlusion balloon and the distal sensor is a pressure sensor configured to measure central aortic pressure upstream of the occlusion balloon.

3. The vascular occlusion catheter of claim 1, wherein the proximal sensor is suspended in a first sensor case sealingly mounted in the second internal lumen, and the distal sensor is suspended in a second sensor case sealingly mounted in the distal internal lumen.

4. The vascular occlusion catheter of claim 1, further comprising an inflation hub in fluid communication with the display hub, the first internal lumen also being in fluid communication with the display hub, wherein the inflation hub is fluidly connected with the first internal lumen within the display hub.

5. The vascular occlusion catheter of claim 1, where the solid distal wire is constructed of nitinol.

6. The vascular occlusion catheter of claim 1, wherein a portion of the solid distal wire overlapping with the hypotube is jacketed to the hypotube.

7. The vascular occlusion catheter of claim 1, where the distal outer section is at least partially constructed of a braided shaft.

8. The vascular occlusion catheter of claim 1, wherein the display hub includes a data transmission port configured for selective wired connection to a remote unit.

9. The vascular occlusion catheter of claim 1, wherein the display hub comprises an internal hub frame securing the hypotube and first internal lumen to the display hub.

10. The vascular occlusion catheter of claim 9, further comprising an inflation hub in fluid communication with the display hub via an inflation shaft, the internal hub frame securing the inflation shaft and fluidly connecting the inflation hub with the first internal lumen.

11. The vascular occlusion catheter of claim 1, wherein the solid distal wire tapers from a proximal end thereof to a distal end thereof.

12. The vascular occlusion catheter of claim 1, wherein the solid distal wire extends beyond a distal end of the hypotube by a distance greater than a greatest outer diameter of the catheter in an uninflated condition.

13. The vascular occlusion catheter of claim 1, wherein the occlusion balloon, the proximal outer section and the distal outer section have a greatest outer diameter of seven French (7 Fr) or less in an uninflated condition.

14. A vascular occlusion catheter for at least partial occlusion of a target vessel having an internal vessel wall, the vascular occlusion catheter comprising:
- an inflation hub having an inflation shaft extending therefrom;
- a proximal outer section;
- a distal outer section;
- a tip at a distal end of the catheter; and
- an occlusion balloon connected to the proximal outer section and the distal outer section;
- the proximal outer section having a first internal lumen and a second internal lumen, the first internal lumen being in fluid communication with the occlusion balloon;
- the distal outer section having a distal internal lumen;
- a hypotube having an internal hypotube lumen, the hypotube extending through the first internal lumen, through the occlusion balloon and into communication with the distal internal lumen, the hypotube operating as the primary load-bearing chassis of the vascular occlusion catheter;
- a solid distal wire embedded in the distal outer section and extending toward the tip, the solid distal wire having a central axis that is radially offset from a central axis of the hypotube;
- a first window formed in the proximal outer section;
- a proximal sensor being positioned within the second internal lumen facing the first window;
- a second window formed in the distal outer section;
- a distal sensor being positioned within the distal internal lumen facing the second window; and
- a display hub positioned along the proximal outer section and having an internal hub frame, (i) the first internal lumen and the hypotube extending into the display hub and being secured to the internal hub frame, (ii) the inflation shaft extending into the display hub and being secured to the internal hub frame, the internal hub frame fluidly connecting the inflation hub with the first internal lumen, (iii) the second internal lumen extending into the display hub, the display hub being electrically connected with the proximal sensor via the second internal lumen, and (iv) the display hub being electrically connected with the distal sensor via the internal hypotube lumen and the distal internal lumen.

15. The vascular occlusion catheter of claim 14, wherein the portion of the solid distal wire overlapping with the hypotube is jacketed to the hypotube.

16. The vascular occlusion catheter of claim 14, wherein the display hub includes a data transmission port configured for selective wired connection to a remote unit.

17. The vascular occlusion catheter of claim 14, wherein the solid distal wire tapers from a proximal end thereof to a distal end thereof.

18. The vascular occlusion catheter of claim 14, wherein the solid distal wire extends beyond a distal end of the hypotube by a distance greater than a greatest outer diameter of the catheter in an uninflated condition.

19. The vascular occlusion catheter of claim 14, wherein the occlusion balloon, the proximal outer section and the distal outer section have a greatest outer diameter of seven French (7 Fr) or less in an uninflated condition.

20. A vascular occlusion catheter for at least partial occlusion of a target vessel having an internal vessel wall, the vascular occlusion catheter comprising:
- a proximal outer section;
- a distal outer section;
- a tip at a distal end of the catheter; and
- an occlusion balloon connected to the proximal outer section and the distal outer section;
- the proximal outer section having a first internal lumen and a second internal lumen, the first internal lumen being in fluid communication with the occlusion balloon;
- the distal outer section having a distal internal lumen;
- a hypotube having an internal hypotube lumen, the hypotube extending through the first internal lumen, through the occlusion balloon and into communication with the distal internal lumen, the hypotube operating as the primary load-bearing chassis of the vascular occlusion catheter;
- a solid distal wire embedded in the distal outer section, the solid distal wire originating distally from a proximal-most end of a proximal neck of the occlusion balloon, extending toward the tip and having a central axis that is radially offset from a central axis of the hypotube;
- a first window formed in the proximal outer section;
- a proximal sensor being positioned within the second internal lumen facing the first window;
- a second window formed in the distal outer section;
- a distal sensor being positioned within the distal internal lumen facing the second window; and
- a display hub positioned along the proximal outer section, wherein the second internal lumen and the hypotube extend into the display hub, the display hub being electrically connected with the proximal sensor via the second internal lumen, and the display hub being electrically connected with the distal sensor via the internal hypotube lumen and the distal internal lumen.

* * * * *